(12) United States Patent
Edens et al.

(10) Patent No.: US 7,608,697 B2
(45) Date of Patent: Oct. 27, 2009

(54) PROTEIN HYDROLYSATES ENRICHED IN PEPTIDES HAVING A CARBOXY TERMINAL PROLINE RESIDUE

(75) Inventors: Luppo Edens, Rotterdam (NL); Robertus Antonius Mijndert Van Der Hoeven, Katwijk (NL); Veronique Delest, Antony (FR)

(73) Assignee: DSM IP Assets B.V., Heerlen (NL)

( * ) Notice: Subject to any disclaimer, the term of this patent is extended or adjusted under 35 U.S.C. 154(b) by 820 days.

(21) Appl. No.: 10/433,747

(22) PCT Filed: Dec. 6, 2001

(86) PCT No.: PCT/EP01/14479

§ 371 (c)(1),
(2), (4) Date: Nov. 10, 2003

(87) PCT Pub. No.: WO02/45523

PCT Pub. Date: Jun. 13, 2002

(65) Prior Publication Data

US 2004/0241791 A1 Dec. 2, 2004

(30) Foreign Application Priority Data

Dec. 7, 2000 (EP) .................... 00204404
Nov. 15, 2001 (EP) .................... 01204464

(51) Int. Cl.
*A61K 38/01* (2006.01)
*C07K 1/12* (2006.01)
*C12P 21/06* (2006.01)
*A23J 3/08* (2006.01)
*A23J 3/34* (2006.01)

(52) U.S. Cl. .................. 530/407; 435/68.1; 435/225
(58) Field of Classification Search .................. None
See application file for complete search history.

(56) References Cited

U.S. PATENT DOCUMENTS

2004/0115306 A1 6/2004 Lopez et al.
2004/0241664 A1 12/2004 Dekker et al.
2004/0241791 A1 12/2004 Edens et al.
2005/0064403 A1 3/2005 Edens et al.

FOREIGN PATENT DOCUMENTS

| EP | 0223 560 | 5/1987 |
|---|---|---|
| EP | 321 603 | 6/1989 |
| EP | 325 986 | 8/1989 |
| JP | 02039896 | 2/1990 |
| JP | 04297923 | 10/1992 |
| JP | 05015314 | * 1/1993 |
| JP | 5-344864 | 12/1993 |
| JP | 7-115969 | 5/1995 |
| JP | 09000164 | 1/1997 |
| JP | 9-310645 | 12/1997 |
| JP | 11-221024 | 8/1999 |
| JP | 11-225686 | 8/1999 |
| JP | 11-243866 | 9/1999 |
| WO | WO 96/13174 | 5/1996 |
| WO | 02/45523 A2 | 6/2002 |
| WO | 02/045523 A3 | 6/2002 |
| WO | 02/45524 A2 | 6/2002 |
| WO | 02/46381 A2 | 6/2002 |
| WO | 02/068623 A2 | 9/2002 |
| WO | 02/045524 A3 | 10/2002 |
| WO | 02/046381 A3 | 11/2002 |
| WO | 02/068623 A3 | 12/2002 |

OTHER PUBLICATIONS

Quemeneur E. et al. "Engineering Cycophilin into a Prolin-Specific Endopeptidase", Jan. 1998, Nature, vol. 391, pp. 301-304.*
Soichi et al. Diazu Tanpakushitsu Eiyo Kenkyukai Kaishi (1985) 6:85-87 (abstract).*
Journal of Dairy Science (1994) 77(2):385-392.
Kuwabara et al., Plant and Cell Physiology (1995) 36(3):435-439.
Kuwabara et al. "Expression in *Escherichia coli* of the extrinsic 18-kDa protein of photosystem II of spinach" Plant Cell Physiol. 36:435-439 (1995).

* cited by examiner

*Primary Examiner*—Cecilia Tsang
*Assistant Examiner*—Christina Bradley
(74) *Attorney, Agent, or Firm*—Nixon & Vanderhye P.C.

(57) ABSTRACT

A method of enzymatically producing a protein hydrolysate from a protein substrate is described, wherein a proline-specific endoprotease or a composition containing a proline-specific endoprotease and optionally a subtilisin or a metallo endoprotease, and other enzymes such as carboxypeptidases, is used to produce a protein hydrolysate enriched in peptide fragments having a carboxy terminal proline residue. Such protein hydrolysates may be used as such or to reduce bitterness in foods nutritionally supplemented by protein hydrolysates, as well as to produce hydrolysate containing foodstuffs having low antigenicity.

23 Claims, 2 Drawing Sheets

PROTEIN HYDROLYSATES ENRICHED IN PEPTIDES HAVING A CARBOXY TERMINAL PROLINE RESIDUE

CROSS-REFERENCE TO RELATED APPLICATION

This application is the national phase of PCT application PCT/EP01/14479 having an international filing date of 6 Dec. 2001, and claims priority from European application EP 00204404.8 filed 7 Dec. 2000. The contents of these documents are incorporated herein by reference.

FIELD OF THE INVENTION

The present invention relates to protein hydrolysates, a method to produce the hydrolysates and the use of these hydrolysates.

BACKGROUND OF THE INVENTION

Enzyme hydrolysates of cow's milk or fractions of cow's milk have only limited application in the food industry. Nevertheless, these hydrolysates occupy interesting niches in the marketplace, as evidenced by the large volume of literature describing and claiming optimised processes for obtaining such hydrolysates. Milk or milk fractions are subjected to enzymes having proteolytic activity to produce the hydrolysates primarily to minimize the allergenicity of the product, facilitate gastrointestinal uptake by offering an easily assimilable digest, and to stabilize the proteins in acid products against precipitation during prolonged storage periods.

Although reducing the molecular weight of milk proteins is commonly accepted practice for producing these beneficial effects, enzymatic hydrolysis of milk proteins does have drawbacks. Negative aspects of incubating milk with enzymes include incomplete proteolytic digestion, an increasingly bitter taste upon decreasing the length of the peptide fragments, decreased yields of the final product due to the requisite purification steps, and unpleasant taste changes caused by high levels of free amino acids.

Uniform and complete degradation of all milk fractions via incubation with endoproteases is often difficult to obtain. For example, beta-lactoglobulin is known to be protease resistant and partial digests of this molecule can lead to unexpectedly strong immunogenic reactions to infant formulae, as well as visible protein precipitations in products such as acidic sport drinks. To guarantee the absence of inadequately digested proteins in a protein hydrolysate, a final ultrafiltration step for the removal of any remaining large peptide fragments from the hydrolysate is generally required. The indispensable step of removing these partially digested protein fragments from the hydrolysate inevitably lowers the yield of the final digestion product, thereby increasing production costs.

Protein antigenicity may be overcome by digesting proteins to peptides having only 8-10 amino acid residues, but the peptides created by such an extensive proteolytic digestion can be very bitter. The general explanation for this phenomenon is that smaller peptides with a high content of hydrophobic amino acids promote bitter tastes. The nature of the proteinaceous raw material used, the type of proteolytic enzymes used for digestion and the length of peptides obtained largely determine the degree of bitterness associated with the final hydrolysate. For example, casein, which contains many hydrophobic amino acids, is known to generate far more bitter hydrolysates than whey proteins.

In industrial operations, debittering of protein hydrolysates is carried out by the selective removal of bitter peptides using activated carbon or adsorption to hydrophobic resin. The concomitant yield reduction during such removal steps increases the cost of the final product. Moreover, this process has a negative impact on the nutritional value of the final product, as several nutritionally indispensable amino acids may be lost due to their hydrophobic nature, including tryptophan, leucine, phenylalanine and isoleucine. Thus, debittering in this way is prone to producing hydrolysates deficient in these nutritionally important amino acids.

Debittering can also be achieved by subjecting hydrolysates to exopeptidases. In this approach, amino-terminal and carboxy-terminal amino acids are liberated from peptides in an attempt to reduce their overall hydrophobicity. Exposure of peptides to non-selective exoproteases unfortunately results in the release of uncontrollable quantities of free amino acids Into the final hydrolysate. Subsequent heating of such hydrolysates containing free amino acids, as required for sterilisation or spray drying, often generates brothy off-flavours via Maillard reactions. Moreover, the high levels of free amino acids created by exoproteases may increase the osmotic value of the final hydrolysate product to levels that can cause osmotic diarrhoea.

Therefore, the production of protein hydrolysates represents a trade-off between the pros and cons of proteolytic digestion. Current practise is to optimize enzymatic digestion of protein substrates for the particular requirements of a product category. For example, protein hydrolysates intended for truly allergic infants require extensive proteolytic digestion followed by a rigorous removal of any remaining large molecular weight peptide fragments. By contrast, products designed for adults, who rarely exhibit bovine milk allergies, typically contain hydrolysates in which the average peptide length is increased to minimize the possibility of off flavours and to maximize product yield.

All major milk proteins, such as beta-casein, beta-lactoglobulin and alpha-lactoalbumin, as well as vegetable protein fractions obtained from, for example, soy isolates, rice proteins and wheat gluten are considered important antigenic compounds. Thus, enzymatic digestion of these milk and cereal proteins to molecular weights below 3000 Da is considered important to minimize allergenicity. The beta-lactoglobulin fraction in whey is especially thought to be an important allergen because this protein is not present in human milk and proteolytic digestion of beta-lactoglobulin has proven to be difficult. Infant formula containing protein hydrolysates that are extensively hydrolyzed typically contain high levels of free amino acids, which are indicative of suboptimal taste and high osmolalities. Recent evaluations of currently marketed hydrolyzed infant formula products have shown that most of them still contain whey based immunogenic materials. This observation indicates that new enzyme mixtures leading to improved hydrolysates at a lower cost continue to be in demand.

Protein hydrolysates in products destined for consumers with non-medical needs, for example athletes or people on a slimming diet, must be tailored to provide good taste characteristics. Under these circumstances, high palatability as well as physico-chemical aspects, such as solubility under acidic conditions, are of overriding importance. Products in this category, including fortified fruit juices and sports drinks, focus on, inter alia, glutamine and arginine supplementation to improve consumer health. Sports drinks, for example, serve to enhance physical endurance and recovery of an athlete after prolonged high intensity exercise. Glutamine-rich cereal protein sources, like wheat gluten, or arginine-rich protein sources, like rice protein and soy isolates, have been considered as alternatives to milk proteins to satisfy the supplementation needs of acidic health-related products. However, such cereal proteins, particularly wheat gluten, exhibit very poor solubilities at more acidic pH values i.e. those above 4, meaning completely soluble gluten hydrolysates are difficult to obtain.

Because of the negative influence on product cost and quality associated with protein hydrolysis, several enzyme mixtures aimed at improving hydrolysate characteristics and lowering production costs have been described in prior publications. Examples include EP 321 603, which refers to the use of animal-derived endoproteases like trypsin, chymotrypsin and pancreatin, and EP 325 986 and WO 96/13174, which favor the use of endoproteases obtained from *Bacillus* or *Aspergillus* species. Several exoproteases have been described as being capable of debittering mixtures of peptides. Whereas, for example, EP 0223 560 refers to the use of a specific proline specific endoprotease, WO 96/13174 refers to a mixture of amino-peptidases and carboxypeptidases for this purpose.

A number of publications tout the beneficial effects of proline-specific endoproteases in combination with various exopeptidases for producing protein hydrolysates which have relatively low bitterness profiles. For example, Japanese patent JP02039896 refers to the use of a proline-specific endoprotease combined with a dipeptidyl-carboxypeptidase for generating low molecular weight peptide preparations. The degradation of proline-rich oligopeptides by three proline-specific peptide hydrolases is described as essential for accelerating cheese ripening without bitterness (Journal of Dairy Science, 77 (2) 385-392 (1994)). More specifically, the debittering effect of proline-specific endoprotease in combination with a carboxypeptidase is described in JP5015314. JP5015314 describes a crude enzyme preparation obtained from *Aspergillus oryzae* that exhibits, apart from a general, non-specific proteolytic activity, small quantities of a proline-specific endoprotease and carboxypeptidase activity. According to JP5015314, proline residues present at the carboxy terminii of peptides cause bitter tastes and are undesirable. Incubation of soy bean protein with a proline-specific endoprotease and carboxypeptidase enzyme mixture yielded a hydrolysate that was significantly less bitter than a soy bean hydolysate obtained with protease preparation lacking the combination of a proline-specific endoprotease and a carboxypeptidase.

Collectively, the state of the art strongly suggests that exopeptidase-mediated release of carboxy terminal (or amino terminal) hydrophobic amino acid residues from peptides is essential for significantly debittering peptide hydrolysates. Likewise, references that specifically refer to proline-specific endoproteases for debittering teach that the function of this activity is to expose the hydrophobic proline residues to allow their subsequent removal by a carboxypeptidase. The implication of this hypothesis is that the debittering activity of proline-specific endoproteases is linked with the efficient removal of the carboxy terminal proline residues rather than the creation of peptides carrying such carboxy terminal proline residues.

SUMMARY OF THE INVENTION

The present invention provides a protein hydrolysate which comprises peptides wherein the molar fraction of peptides (%) carrying a carboxy terminal proline is more than two times higher than the molar fraction (%) of proline in the protein substrate used to generate the hydrolysate.

The present invention also provides:

a whey hydrolysate which comprises peptides wherein the molar fraction of peptides carrying a carboxy terminal proline is at least 8%, preferably at least 15%, more preferably from 30 to 70%;

a casein hydrolysate which comprises peptides wherein the molar fraction of peptide carrying a carboxy terminal proline is at least 25%, preferably at least 30% and more preferably less than 70%;

a soy hydrolysate which comprises peptides wherein the molar fraction of peptide carrying a carboxy terminal proline is at least 20%, preferably from 30 to 70%.

a gluten hydrolysate which comprises peptides wherein the molar fraction of peptide carrying a carboxy terminal proline is at least 20%, preferably at least 30%, advantageously less than 70%; and a barley hydrolysate which comprises peptides wherein the molar fraction of peptide carrying a carboxy terminal proline is at least 20%, preferably at least 30%, advantageously less than 70%.

The present invention further provides a proline-specific endoprotease selected from the group consisting of:

(a) a polypeptide which has an amino acid sequence which has at least 40% amino acid sequence identity with amino acids 1 to 526 of SEQ ID NO:2 or a fragment thereof;

(b) a polypeptide which is encoded by a polynucleotide which hybridizes under low stringency conditions with (i) the nucleic acid sequence of SEQ ID NO:1 or a fragment thereof which is at least 80% or 90% Identical over 60, preferably over 100 nucleotides more preferably at least 90% identical over 200 nucleotides, or (ii) a nucleic acid sequence complementary to the nucleic acid sequence of SEQ ID NO: 1.

and a DNA molecule encoding the endopeptidase.

The present invention also provides:

the use of a protein hydrolysate of the invention in a food or drink;

the use of a proline-specific endoprotease according to the invention;

a method of enzymatically producing a protein hydrolysate from a protein substrate, wherein the protein substrate is incubated with a proline-specific endoprotease to produce a protein hydrolysate enriched in peptides having a carboxy terminal proline;

an enzyme composition comprising a proline-specific endoprotease of the invention, the composition being capable of producing a protein hydrolysate comprising peptides, wherein the molar fraction of peptides (%) carrying a carboxy terminal proline is at least two times the molar fraction (%) of proline in the protein or a hydrolysate of the invention; and a food comprising a protein hydrolysate of the invention or obtainable by a method of the invention.

DETAILED DESCRIPTION OF THE INVENTION

Figure 1:
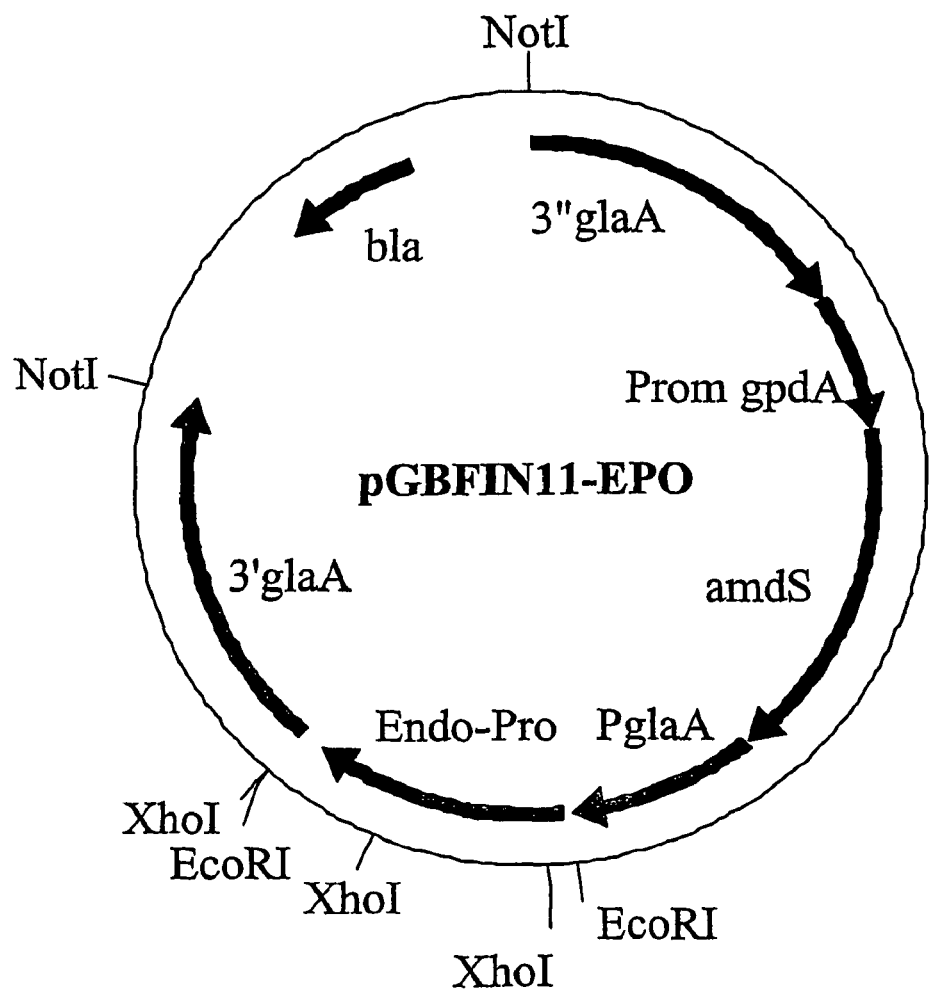
FIG. 1 illustrates a map of expression plasmid pGBFIN11-EPO. Endo-Pro stands for the proline specific endoprotease.

We have shown that a high incidence of proline residues at the carboxy terminal end of peptides can be correlated with low bitterness. Moreover we have demonstrated that the desired high incidence of carboxy terminal proline residues can only be achieved with high concentrations of a proline-specific endoprotease, i.e. concentrations that exceed the activity specified in JP5015314 by several orders of magnitude and moreover in the absence of a carboxypeptidase.

From an economic point of view the implication of this observation is that there exists a clear need for an improved means of producing proline-specific endoproteases in high quantities and a relatively pure form. A preferred way of doing this is via the overproduction of such a proline-specific endoprotease using recombinant DNA techniques. As many food products are acidic and long term enzyme incubations under industrial, non-sterile circumstances require acidic incubation conditions to prevent microbial contamination, a more preferred way of doing this is via the overproduction of an acid stable proline-specific endoprotease using recombinant DNA techniques. A particularly preferred way of doing this is via the overproduction of an *Aspergillus* derived proline-specific endoprotease and a most preferred way of doing this is via the overproduction of an *Aspergillus niger* derived proline-specific endopeptidase. To enable the latter route unique sequence information of an *Aspergillus* derived proline-specific endoprotease is essential. More preferable the whole nucleotide sequence of the encoding gene has to be available.

Once the new enzyme has been made available in a relatively pure form, other new and surprising applications are envisaged which have technical and economical advantages. A new application would be the creation of non-bitter hydrolysates from proteinaceous substrates with unusual amino acid compositions. Such unusual amino acid compositions may offer serious benefits in certain food applications. Examples are casein or wheat gluten or maize protein isolate with high levels of hydrophobic amino acid residues present. Hitherto such substrates were of no practical use because of the objectionable bitter tastes generated upon hydrolysis using prior art methods. Using the hydrolysis method according to the invention, new, non-bitter hydrolysates can be made available to be used in infant and clinical nutrition, in therapeutic diets as well as in consumer diets and sport nutrition. Apart from such new hydrolysates, applications that take advantage of the bitterness reducing effect of the acid proline-specific endoproteases as such are also envisaged. For example, the incorporation of the endopeptidase in proteinaceous food products involving a fermentation step such as in cheeses or yogurt to suppress the bitterness which can evolve upon aging. Also in proteinaceous food products requiring treatment with proteases such as the production of enzyme modified cheeses or the production of protein hydrolysates for the flavour industry, the incorporation of the enzyme according to the invention will help to suppress bitterness.

Moreover, benefits not directly related to suppressing bitter tastes are also investigated. One such new application is the incubation of the enzyme with food proteins to reduce their allergenicity. Several food proteins contain highly allergenic subfractions, such as wheat gluten that contains prolamines with proline-rich peptide sequences. These proteins can be subjected to the new enzyme to alleviate their antigenicity. Another new application is the incorporation of the enzyme in all kinds of doughs as it has been observed that this retards the staling of the breads obtained. Another new application is the use of the proline specific endoprotease to generate proline rich peptides. Such proline-rich peptides are desirable additions to various food or nutraceutical products as they have been implicated in anorectic action, in fibrinolytic and antithrombotic and antihypertensive effects, in protection of the gastric mucosa as well as the prevention of rheumatoid arthritis.

Another surprising application is addition of the new enzyme to animal feed to enhance protein utilisation. For example, addition of the enzyme leads to improved digestibility of hard-to-digest proline rich sequences present in the feed protein as well as to improved conversion rates of cheaply available vegetable proteins containing high levels of polyphenols.

In yet another new application the enzyme is used in beer brewing. Barley proteins are rich in proline rich sequences and in their non-malted form cereal proteins are extremely difficult to degrade into the free amino acids required to create a suitable fermentable wort. Quite surprisingly the incorporation of the new enzyme into the mashing process has been shown to stimulate amino acid release from milled but non-malted barley so that a much richer wort is obtained. In a similar way beer fermentation from mashes containing a high proportion of other cheap and locally available cereals such as for example sorghum can be improved.

In most of these new applications the proline-specific endoprotease should preferably exhibit an activity spectrum with an acidic pH optimum.

To overcome the above-mentioned problems, the invention demonstrates that the activity of an isolated, purified proline-specific endoprotease alone, i.e. without the substantial concomitant or subsequent activity of an exoproteolytic enzyme, is sufficient for significantly debittering a protein hydrolysate. Therefore the proline-specific endoprotease may comprise at least 5 units per gram protein of the enzyme preparation of the invention, preferably 10 u/g, more preferably 25 u/g and even more preferably 50 u/g Moreover, studies conducted in accordance with the invention demonstrate that the activity of an isolated, purified proline-specific endoprotease alone, meaning without the concomitant or subsequent activity of an exoproteolytic enzyme, is sufficient to significantly decrease the overall immunogenicity level of protein hydrolysates, as well as to significantly increase their overall solubility under acidic conditions. The hydrolysates produced according to the invention are enriched in peptides having a carboxy terminal proline residue.

An embodiment of the present invention provides an enzyme mixture comprising an isolated, purified proline-specific endoprotease for the high yield production of protein hydrolysates having substantially low bitterness and low allergenic properties without the concomitant production of substantial levels of free amino acids. This enzyme mixture is suitable for preparing hydrolysates of various protein fractions. In particular, a protein substrate, such as a milk protein, may be incubated with an isolated, purified proline-specific endoprotease and a subtilisin to produce a protein hydrolysate enriched in peptide fragments having a carboxy terminal proline. The term "enriched" is intended to mean that at least 8% of the peptide fragments in the hydrolysate product of enzymatic cleavage possess a carboxy terminal proline residue.

The present invention provides a protein hydrolysate obtained by hydrolysing a protein which comprises peptides wherein the molar fraction of peptides (%) carrying a carboxy terminal proline is at least two times the molar fraction (%) of proline in the protein substrate used to produce the hydrolysate. The average length of the peptides in the hydrolysates is in general from 3 to 9 amino acids.

Preferred hydrolysates according to the invention are: a whey hydrolysate which comprises peptides wherein the molar fraction of peptides carrying a carboxy terminal proline is at least 8%, preferably at least 15%, more preferably from 30 to 70%, a casein hydrolysate which comprises peptides wherein the molar fraction of peptide carrying a carboxy terminal proline is at least 25%, preferably from 30 to 70%, and a soy hydrolysate which comprises peptides wherein the molar fraction of peptides carrying a carboxy terminal proline is at least 20%, preferably from 30 to 70%.

By peptides or peptide fragments it is meant peptides with molecular masses from 400 to 2000 Dalton. These peptides can be analysed according to the LC/MC analysis as described the "Materials and Methods" section.

In general in the production of the protein hydrolysates of the invention the protein substrate is substantially hydrolysed, advantageously for at least 50%. Preferably at least 10% of the protein substrate is converted into peptides having molecular masses from 400 to 2000 Dalton. More preferably from 20 to 90% and even more preferably from to 80% of the protein substrate is converted into such peptides.

In another embodiment of the invention, a protein substrate may be incubated with an enzyme mixture comprising an isolated, purifies proline-specific endoprotease, a serine endoprotease or a metallo endoprotease and a carboxypeptidase to produce a protein hydrolysate enriched in peptide fragments having a carboxy terminal proline.

The enzyme mixture of the invention is particularly suitable for use in the production of protein hydrolysates intended for flavoring and nutrient enhancement of sport drinks and juice-based beverages, as the resulting hydrolyzed peptide mixture combines a very low bitterness profile with excellent solubility under the prevailing acidic conditions of such beverages. The enzyme mixture of the invention is characterised in that it contains at least one endoprotease for example a serine protease or a metallo endoprotease in conjunction with a proline-specific endoprotease (E.C. 3.4.21.26) to provide a primary hydrolysate. More specifically, the invention relates to an isolated, purified proline-specific endoprotease and a serine protease or metallo protease enzyme mixture capable of producing a protein hydrolysate comprising peptide fragments, wherein at least 8%, preferably at least 15%, more preferably from 30 to 70% of said peptide fragments have a carboxy terminal proline.

Another embodiment of the invention is a protein hydrolysate enriched with a relatively high content of peptides having proline as the carboxy terminal amino acid residue. Such enriched hydrolysates may comprise at least 8%, preferably at least 15%, more preferably from 30 to 70% peptide fragments having a carboxy terminal proline residue. Since enzyme preparations typically utilized in the genesis of protein hydrolysates are not capable of generating peptides bearing proline residues at carboxy terminii, protein hydrolysates that are relatively rich in such peptides are novel.

Substrates for hydrolysis by an enzyme mixture of the invention include whole milk, skimmed milk, acid casein, rennet casein, acid whey products or cheese whey products. Quite surprisingly the *Aspergillus* derived proline specific endoprotease does not only cleave at the carboxy-terminal side of proline residues but also at the carboxy-terminal side of hydroxyproline residues which makes other, collagen based animal proteins such as gelatine as well as bones or fish-bones containing residual meat, interesting substrates for the enzyme. Moreover, vegetable substrates like wheat gluten, milled barley and protein fractions obtained from, for example, soy, rice or corn are suitable substrates. Milk protein hydrolysates produced according to the invention may be used with or without additional filtration or purification steps in various speciality foods such as hypoallergenic hydrolysates for infant nutrition, basic hydrolysates for enteral and dietetic nutrition, as well as protein concentrates for various forms of health food. Thus, protein hydrolysates of the invention may be used to produce foodstuffs having low antigenicity, such as infant formula. In addition, enzyme preparations according to the invention may be used to reduce bitterness in foods flavored by at least one protein hydrolysate, even when the protein hydrolysate is present in large amounts. For example, foods may comprise between 5% and 10% (w/v) of a protein hydrolysate and still have their bitterness reduced using an enzyme preparation of the invention.

The present invention provides an isolated, purified proline-specific endoprotease with an acidic pH optimum alone or in a composition comprising one or more additional enzymes for the preparation of a protein hydrolysate for various food applications. Such an isolated, purified proline-specific endoprotease is defined to have at least 10 units of proline specific endoprotease activity per gram of proteinaceous material. These units should be measured using the synthetic peptide Z-Gly-Pro-pNA at 37 degrees C. and pH 5 in case the pH optimum of the proline-specific endoprotease is below pH 6, for example in case of *Aspergillus niger* proline specific endo protease or else the units should be measured at pH=7, as specified in the Materials and Methods section. This isolated, purified enzyme, alone or in an enzyme mixture, overcomes a number of disadvantages of enzyme mixtures previously known in the art. Most importantly, the inventive isolated, purified proline-specific endoprotease is key in the production of hydrolysates which combine a low allergenic potential, a high yield and a low bitterness profile. Moreover, the hydrolysates produced with the isolated, purified proline-specific endoprotease or an enzyme mixture comprising this proline-specific endoprotease are acid stable and contain very low levels of free amino acids, such that minimal off-tastes are generated during heating steps, such as spray drying or product sterilisation. Hydrolysates according to the invention will contain less than 900 micromoles of free amino acids per gram of dry powder, preferably less than 300 micromoles of free amino acids per gram of dry powder, more preferably less than 150 micromoles of free amino acids per gram of dry powder, and even more preferably less than 50 micromoles per gram of dry powder.

The enzyme mixture according to the invention is characterised in that it comprises another endoprotease such as a serine protease or a metallo endoprotease in conjunction with an isolated, purified proline-specific endoprotease (E.C. 3.4.21.26) which work together to provide a primary protein hydrolysate.

Serine proteases represent a well known class of alkaline endoproteases and some of its most important representatives such as subtilisin (E.C. 3.4.21.62) and chymotrypsin (E.C. 3.4.21.1) prefer cleavage of the peptide chain at the carboxy terminal side of hydrophobic amino acids such as Tyr, Trp, Phe and Leu. The enzyme mixture of the invention may contain chymotrypsin and/or subtilisin. Subtilisin is produced by species of *Bacillus*, has a particularly broad substrate specificity and a broad, alkaline pH optimum. The enzyme is optimally active between 50° C. and 60° C. The enzyme is cheaply available as a regular commercial product and is useful in the production of, for example, various milk hydrolysates. Chymotrypsin may be obtained from animal pancreases, has a somewhat narrower substrate specificity at slightly more alkaline pH values than subtilisin and is optimally active below 50 degrees C.

The class of metallo endoproteases is wide spread in bacteria, fungi and higher organisms. They can be separated into the neutral and acid metalloproteases. Of these two subclasses only the neutral proteases exhibit the desirable cleavage preference I.e. cleaving the peptide chain on the carboxy terminal side of hydrophobic amino acid residues such as Phe and Leu. Well known representatives of the category of the neutral metallo proteases are bacillolysin (E.C. 3.4.24.28) and thermolysin (E.C. 3.4.24.27) and either, or both of these, may be present in the enzyme mixture of the invention. Both enzymes are obtained from *Bacillus* species and exhibit maximum activity under neutral or slightly alkaline conditions. Less well known representatives of these neutral metallo endoproteases have been obtained from *Aspergillus* species. In those cases in which the proline specific endoprotease is not used for its debittering effects but to aid in the hydrolysis of proline rich protein sequences, combinations with the class of the acid metalloproteases, as for example deuterolysine (EC 3.4.24.39) can be advantageous. A proline-specific endoprotease is an endoprotease capable of cleaving peptides or polypeptides at the carboxy-terminal end of proline residues. Such enzymes are widely found in animals and plants, but their presence in microorganisms appears to be limited. To date, proline-specific endoprotease have been identified in species of *Aspergillus* (EP 0 522 428), *Flavobacterium* (EP 0 967 285) and *Aeromonas* (J.Biochem.113, 790-796), *Xanthomonas* and *Bacteroides*. Though the proline-specific enzymes from most of these organisms are active around pH 8, the *Aspergillus* enzyme is optimally active around pH 5. According to a preferred embodiment, proline-specific endoprotease having a pH optimum below 7, preferably having a pH optimum from 3.5 to 6.5 is used because of the technical and economical advantages of such enzymes. The proline-specific endoprotease of the invention may be isolated from one of the above-mentioned microbial species, particularly from a species of *Aspergillus*. Preferably, the proline-specific endoprotease is isolated from a strain of *Aspergillus niger*. More preferably, the proline-specific endoprotease is isolated from an *Aspergillus niger* host engineered to overexpress a gene encoding a proline-specific endoprotease, although other hosts, such as *E. coli* are suitable expression vectors. For example, the cloning and overproduction of the *Flavobacterium* derived proline-specific endoprotease in, amongst others, *E. coli* has made certain proline-specific endoproteases available in a pure form. An example of such an overproducing construct is provided in the World Journal of Microbiology & Biotechnology, Vol 11,pp 209-212. An *Aspergillus niger* host is preferably used to produce a non-recombinant self-construct utilizing *A. niger* promoters to drive the expression of a gene encoding an *A. niger* proline-specific endoprotease.

Most of the scientific publications concerning the cloning and production of proline-specific-endoproteases focus on the role of this enzyme in the synthesis and regulation of biologically active proteins. Publications implicating this enzyme in the production of useful protein hydrolysates are scarce and are concerned with the use of the enzyme in conjunction with an exoprotease. Several Japanese publications refer to the presence of proline-specific-endoproteolytic activity in crude and complex enzyme mixtures capable of producing hydrolysates with low bitterness profiles, but the enzyme mixtures used always contain exoproteases. No direct connection between debittering and proline-specific endoproteolytic activity in the absence of exoproteases like carboxypeptidases or aminopeptidases is suggested in the art. Moreover, no data linking hydrolysates produced using proline-specific-endoproteolytic activity with a diminished immunogenic response or an improved acid solubility has been previously described.

A polypeptide of the invention which has proline specific endoprotease may be in an isolated form. As defined herein, an isolated polypeptide is an endogenously produced or a recombinant polypeptide which is essentially free from other non-proline specific endoprotease polypeptides, and is typically at least about 20% pure, preferably at least about 40% pure, more preferably at least about 60% pure, even more preferably at least about 80% pure, still more preferably about 90% pure, and most preferably about 95% pure, as determined by SDS-PAGE. The polypeptide may be isolated by centrifugation and chromatographic methods, or any other technique known in the art for obtaining pure proteins from crude solutions. It will be understood that the polypeptide may be mixed with carriers or diluents which do not interfere with the intended purpose of the polypeptide, and thus the polypeptide in this form will still be regarded as isolated. It will generally comprise the polypeptide in a preparation in which more than 20%, for example more than 30%, 40%, 50%, 80%, 90%, 95% or 99%, by weight of the proteins in the preparation is a polypeptide of the invention.

Preferably, the polypeptide of the invention is obtainable from a microorganism which possesses a gene encoding an enzyme with proline specific endoprotease activity. More preferably the microorganism is fungal, and optimally is a filamentous fungus. Preferred organisms are thus of the genus *Aspergillus*, such as those of the species *Aspergillus niger*.

In a first embodiment, the present invention provides an isolated polypeptide having an amino acid sequence which has a degree of amino acid sequence identity to amino acids 1 to 526 of SEQ ID NO: 2 (i.e. the polypeptide) of at least about 40%, preferably at least about 50%, preferably at least about 60%, preferably at least about 65%, preferably at least about 70%, more preferably at least about 80%, even more preferably at least about 90%, still more preferably at least about 95%, and most preferably at least about 97%, and which has proline specific endoprotease activity.

For the purposes of the present invention, the degree of identity between two or more amino acid sequences is determined by BLAST P protein database search program (Altschul et al., 1997, Nucleic Acids Research 25: 3389-3402) with matrix Blosum 62 and an expected threshold of 10.

A polypeptide of the invention may comprise the amino acid sequence set forth in SEQ ID NO: 2 or a substantially homologous sequence, or a fragment of either sequence having proline specific endoprotease activity. In general, the naturally occurring amino acid sequence shown in SEQ ID NO: 2 is preferred.

The polypeptide of the invention may also comprise a naturally occurring variant or species homologue of the polypeptide of SEQ ID NO: 2.

A variant is a polypeptide that occurs naturally in, for example, fungal, bacterial, yeast or plant cells, the variant having proline specific endoprotease activity and a sequence substantially similar to the protein of SEQ ID NO: 2. The term "variants" refers to polypeptides which have the same essential character or basic biological functionality as the proline specific endoprotease of SEQ ID NO: 2, and includes allelic variants. The essential character of proline specific endoprotease of SEQ ID NO: 2 is that it is an enzyme capable of cleaving the amino-terminal amino acid from a protein or (poly)peptide. Preferably, a variant polypeptide has at least the same level of proline specific endoprotease activity as the polypeptide of SEQ ID NO: 2. Variants include allelic variants either from the same strain as the polypeptide of SEQ ID NO:2 or from a different strain of the same genus or species.

Similarly, a species homologue of the inventive protein is an equivalent protein of similar sequence which is an proline specific endoprotease and occurs naturally in another species of *Aspergillus*.

Variants and species homologues can be isolated using the procedures described herein which were used to isolate the polypeptide of SEQ ID NO: 2 and performing such procedures on a suitable cell source, for example a bacterial, yeast, fungal or plant cell. Also possible is to use a probe of the invention to probe libraries made from yeast, bacterial, fungal or plant cells in order to obtain clones expressing variants or species homologues of the polypepetide of SEQ ID NO: 2. These clones can be manipulated by conventional techniques to generate a polypeptide of the invention which thereafter may be produced by recombinant or synthetic techniques known per se.

The sequence of the polypeptide of SEQ ID NO: 2 and of variants and species homologues can also be modified to provide polypeptides of the invention. Amino acid substitutions may be made, for example from 1, 2 or 3 to 10, 20 or 30 substitutions. The same number of deletions and insertions may also be made. These changes may be made outside regions critical to the function of the polypeptide, as such a modified polypeptide will retain its proline specific endoprotease activity.

Polypeptides of the invention include fragments of the above mentioned full length polypeptides and of variants thereof, including fragments of the sequence set out in SEQ ID NO: 2. Such fragments will typically retain activity as an proline specific endoprotease. Fragments may be at least 50, 100 or 200 amino acids long or may be this number of amino acids short of the full length sequence shown in SEQ ID NO: 2.

Polypeptides of the invention can, if necessary, be produced by synthetic means although usually they will be made recombinantly as described below. Synthetic polypeptides may be modified, for example, by the addition of histidine residues or a T7 tag to assist their identification or purification, or by the addition of a signal sequence to promote their secretion from a cell.

Thus, the variants sequences may comprise those derived from strains of *Aspergillus* other than the strain from which the polypeptide of SEQ ID NO: 2 was isolated. Variants can be identified from other *Aspergillus* strains by looking for proline specific endoprotease activity and cloning and sequencing as described herein. Variants may include the deletion, modification or addition of single amino acids or groups of amino acids within the protein sequence, as long as the peptide maintains the basic biological functionality of the proline specific endoprotease of SEQ ID NO: 2.

Amino acid substitutions may be made, for example from 1, 2 or from 3 to 10, 20 or 30 substitutions. The modified polypeptide will generally retain activity as an proline specific endoprotease. Conservative substitutions may be made; such substitutions are well known in the art. Preferably substitutions do not affect the folding or activity of the polypeptide.

Shorter polypeptide sequences are within the scope of the invention. For example, a peptide of at least 50 amino acids or up to 60, 70, 80, 100, 150 or 200 amino acids in length is considered to fall within the scope of the invention as long as it demonstrates the basic biological functionality of the proline specific endoprotease of SEQ ID NO: 2. In particular, but not exclusively, this aspect of the invention encompasses the situation in which the protein is a fragment of the complete protein sequence.

In a second embodiment, the present invention provides an to isolated polypeptide which has proline specific endoprotease activity, and is encoded by polynucleotides which hybridize or are capable of hybrizing under low stringency conditions, more preferably medium stringency conditions, and most preferably high stringency conditions, with (i) the nucleic acid sequence of SEQ ID NO: 1 or a nucleic acid fragment comprising at least the c-terminal portion of SEQ ID NO: 1, but having less than all or having bases differing from the bases of SEQ ID NO: 1; or (ii) with a nucleic acid strand complementary to SEQ ID NO: 1.

The term "capable of hybridizing" means that the target polynucleotide of the invention can hybridize to the nucleic acid used as a probe (for example, the nucleotide sequence set forth in SEQ. ID NO: 1, or a fragment thereof, or the complement of SEQ ID NO: 1) at a level significantly above background. The invention also includes the polynucleotides that encode the proline specific endoprotease of the invention, as well as nucleotide sequences which are complementary thereto. The nucleotide sequence may be RNA or DNA, including genomic DNA, synthetic DNA or cDNA. Preferably, the nucleotide sequence is DNA and most preferably, a genomic DNA sequence. Typically, a polynucleotide of the invention comprises a contiguous sequence of nucleotides which is capable of hybridizing under selective conditions to the coding sequence or the complement of the coding sequence of SEQ ID NO: 1. Such nucleotides can be synthesized according to methods well known in the art.

A polynucleotide of the invention can hybridize to the coding sequence or the complement of the coding sequence of SEQ ID NO:1 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1 is typically at least 10 fold, preferably at least 20 fold, more preferably at least 50 fold, and even more preferably at least 100 fold, as intense as interactions between other polynucleotides and the coding sequence of SEQ ID NO: 1. The intensity of interaction may be measured, for example, by radiolabelling the probe, for example with $^{32}$P. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60° C.).

Modifications

Polynucleotides of the invention may comprise DNA or RNA. They may be single or double stranded. They may also be polynucleotides which include within them synthetic or modified nucleotides including peptide nucleic acids. A number of different types of modifications to polynucleotides are known in the art. These include a methylphosphonate and phosphorothioate backbones, and addition of acridine or polylysine chains at the 3' and/or 5' ends of the molecule. For the purposes of the present invention, It is to be understood that the polynucleoudes described herein may be modified by any method available in the art.

It is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

The coding sequence of SEQ ID NO: 1 may be modified by nucleotide substitutions, for example from 1, 2 or 3 to 10, 25, 50 or 100 substitutions. The polynucleotide of SEQ ID NO: 1 may alternatively or additionally be modified by one or more insertions and/or deletions and/or by an extension at either or both ends. The modified polynucleotide generally encodes a polypeptide which has proline specific endoprotease activity. Degenerate substitutions may be made and/or substitutions may be made which would result in a conservative amino acid substitution when the modified sequence is translated, for example as discussed with reference to polypeptides later.

Homologues

A nucleotide sequence which is capable of selectively hybridizing to the complement of the DNA coding sequence of SEQ ID NO: 1 is included in the invention and will generally have at least 50% or 60%, at least 70%, at least 80%, at least 90%, at least 95%, at least 98% or at least 99% sequence identity to the coding sequence of SEQ ID NO: 1 over a region of at least 60, preferably at least 100, more preferably at least 200 contiguous nucleotides or most preferably over the full length of SEQ ID NO: 1. Likewise, a nucleotide which encodes an active proline specific endoprotease and which is capable of selectively hybridizing to a fragment of a complement of the DNA coding sequence of SEQ ID NO: 1, is also embraced by the invention. A C-terminal fragment of the nucleic acid sequence of SEQ ID NO:1 which is at least 80% or 90% identical over 60, preferably over 100 nucleotides, more preferably at least 90% identical over 200 nucleotides is encompassed by the invention.

Any combination of the above mentioned degrees of identity and minimum sizes may be used to define polynucleotides of the invention, with the more stringent combinations (i.e. higher identity over longer lengths) being preferred. Thus, for example, a polynucleotide which is at least 80% or 90% identical over 60, preferably over 100 nucleotides, forms one aspect of the invention, as does a polynucleotide which is at least 90% identical over 200 nucleotides.

The UWGCG Package provides the BESTFIT program which may be used to calculate identity (for example used on its default settings).

The PILEUP and BLAST N algorithms can also be used to calculate sequence identity or to line up sequences (such as identifying equivalent or corresponding sequences, for example on their default settings).

Software for performing BLAST analyses is publicly available through the National Center for Biotechnology Information (http://www.ncbi.nim.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold. These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix alignments (B) of 50, expectation (E) of 10, M=5, N=4, and a comparison of both strands.

The BLAST algorithm performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Primers and Probes

Polynucleotides of the invention include and may be used as primers, for example as polymerase chain reaction (PCR) primers, as primers for alternative amplification reactions, or as probes for example labelled with a revealing label by conventional means using radioactive or non-radioactive labels, or the polynucleotides may be cloned into vectors. Such primers, probes and other fragments will be at least 15, for example at least 20, 25, 30 or 40 nucleotides in length. They will typically be up to 40, 50, 60, 70, 100, 150, 200 or 300 nucleotides in length, or even up to a few nucleotides (such as 5 or 10 nucleotides) short of the coding sequence of SEQ ID NO: 1.

In general, primers will be produced by synthetic means, involving a step-wise manufacture of the desired nucleic acid sequence one nucleotide at a time. Techniques for accomplishing this using automated protocols are readily available in the art. Longer polynucleotides will generally be produced using recombinant means, for example using PCR cloning techniques. This will involve making a pair of primers (typically of about 15-30 nucleotides) to amplify the desired region of the proline specific endoprotease to be cloned, bringing the primers into contact with mRNA, cDNA or genomic DNA obtained from a yeast, bacterial, plant, prokaryotic or fungal cell, preferably of an *Aspergillus* strain, performing a polymerase chain reaction under conditions suitable for the amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the polynucleotides encoding the proline specific endoprotease sequences described herein. Introns, promoter and trailer regions are within the scope of the invention and may also be obtained in an analogous manner (e.g. by recombinant means, PCR or cloning techniques), starting with genomic DNA from a fungal, yeast, bacterial plant or prokaryotic cell.

The polynucleotides or primers may carry a revealing label. Suitable labels include radioisotopes such as $^{32}P$ or $^{35}S$, enzyme labels, or other protein labels such as biotin. Such labels may be added to polynucleotides or primers of the invention and may be detected using techniques known to persons skilled in the art.

Polynucleotides or primers (or fragments thereof) labelled or unlabelled may be used in nucleic acid-based tests for detecting or sequencing an proline specific endoprotease or a variant thereof in a fungal sample. Such detection tests will generally comprise bringing a fungal sample suspected of containing the DNA of interest into contact with a probe comprising a polynucleotide or primer of the invention under hybridizing conditions, and detecting any duplex formed between the probe and nucleic acid in the sample. Detection may be achieved using techniques such as PCR or by immobilizing the probe on a solid support, removing any nucleic acid in the sample which is not hybridized to the probe, and then detecting any nucleic acid which is hybridized to the probe. Alternatively, the sample nucleic acid may be immobilized on a solid support, the probe hybridized and the amount of probe bound to such a support after the removal of any unbound probe detected.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridizing the probe to nucleic acid in the sample, control reagents, instructions, and the like. The probes and polynucleotides of the invention may also be used in microassay.

Preferably, the polynucleotide of the invention is obtainable from the same organism as the polypeptide, such as a fungus, in particular a fungus of the genus *Aspergillus*.

The polynucleotides of the invention also include variants of the sequence of SEQ ID NO: 1 which encode for a polypeptide having proline specific endoprotease activity. Variants may be formed by additions, substitutions and/or deletions. Such variants of the coding sequence of SEQ ID NO:1 may thus encode polypeptides which have the ability to digest a polypeptide chain at the carboxyterminal side of proline.

Production of Polynucleotides

Polynucleotides which do not have 100% identity with SEQ ID NO: 1 but fall within the scope of the invention can be obtained in a number of ways. Thus, variants of the proline specific endoprotease sequence described herein may be obtained for example, by probing genomic DNA libraries made from a range of organisms, such as those discussed as sources of the polypeptides of the invention. In addition, other fungal, plant or prokaryotic homologues of proline specific endoprotease may be obtained and such homologues and fragments thereof in general will be capable of hybridising to SEQ ID NO: 1. Such sequences may be obtained by probing cDNA libraries or genomic DNA libraries from other species, and probing such libraries with probes comprising all or part of SEQ ID. 1 under conditions of low, medium to high stringency (as described earlier). Nucleic add probes comprising all or part of SEQ ID NO: 1 may be used to probe cDNA or genomic libraries from other species, such as those described as sources for the polypeptides of the invention.

Species homologues may also be obtained using degenerate PCR, which uses primers designed to target sequences within the variants and homologues which encode conserved amino acid sequences. The primers can contain one or more degenerate positions and will be used at stringency conditions lower than those used for cloning sequences with single sequence primers against known sequences.

Alternatively, such polynucleotides may be obtained by site directed mutagenesis of the proline specific endoprotease sequences or variants thereof. This may be useful where, for example, silent codon changes to sequences are required to optimize codon preferences for a particular host cell in which the polynucleotide sequences are being expressed. Other sequence changes may be made in order to introduce restriction enzyme recognition sites or to alter the property or function of the polypeptides encoded by the polynucleotides.

The invention includes double stranded polynucleotides comprising a polynucleotide of the invention and its complement.

The present invention also provides polynucleotides encoding the polypeptides of the invention described above. Since such polynucleotides will be useful as sequences for recombinant production of polypeptides of the invention, it is not necessary for them to be capable of hybridising to the sequence of SEQ ID NO: 1, although this will generally be desirable. Otherwise, such polynucleotides may be labelled, used, and made as described above if desired.

Recombinant Polynucleotides.

The invention also provides vectors comprising a polynucleotide of the invention, including cloning and expression vectors, and in another aspect methods of growing, transforming or transfecting such vectors into a suitable host cell, for example under conditions in which expression of a polypeptide of, or encoded by a sequence of, the invention occurs. Provided also are host cells comprising a polynucleotide or vector of the invention wherein the polynucleotide is heterologous to the genome of the host cell. The term "heterologous", usually with respect to the host cell, means that the polynucleotide does not naturally occur in the genome of the host cell or that the polypeptide is not naturally produced by that cell. Preferably, the host cell is a yeast cell, for example a yeast cell of the genus *Kluyveromyces* or *Saccharomyces* or a filamentous fungal cell, for example of the genus *Aspergillus*.

Polynucleotides of the invention can be incorporated into a recombinant replicable vector, for example a cloning or expression vector. The vector may be used to replicate the nucleic acid in a compatible host cell. Thus, in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Vectors

The vector into which the expression cassette of the invention is inserted may be any vector that may conveniently be subjected to recombinant DNA procedures, and the choice of the vector will often depend on the host cell into which it is to be introduced. Thus, the vector may be an autonomously replicating vector, i.e. a vector which exists as an extra-chromosomal entity, the replication of which is independent of chromosomal replication, such as a plasmid. Alternatively, the vector may be one which, when introduced into a host cell, is integrated into the host cell genome and replicates together with the chromosome(s) into which it has been integrated.

Preferably, when a polynucleotide of the invention is in a vector it is operably linked to a regulatory sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under conditions compatible with the control sequences.

The vectors may, for example in the case of plasmid, cosmid, virus or phage vectors, be provided with an origin of replication, optionally a promoter for the expression of the polynucleotide and optionally an enhancer and/or a regulator of the promoter. A terminator sequence may be present, as may be a polyadenylation sequence. The vectors may contain one or more selectable marker genes, for example an ampicillin resistance gene in the case of a bacterial plasmid or a neomycin resistance gene for a mammalian vector. Vectors may be used in vitro, for example for the production of RNA or can be used to transfect or transform a host cell.

The DNA sequence encoding the polypeptide is preferably introduced into a suitable host as part of an expression construct in which the DNA sequence is operably linked to expression signals which are capable of directing expression of the DNA sequence in the host cells. For transformation of the suitable host with the expression construct transformation procedures are available which are well known to the skilled person. The expression construct can be used for transformation of the host as part of a vector carrying a selectable marker, or the expression construct is co-transformed as a separate molecule together with the vector carrying a selectable marker. The vectors may contain one or more selectable marker genes.

Preferred selectable markers include but are not limited to those that complement a defect in the host cell or confer resistance to a drug. They include for example versatile marker genes that can be used for transformation of most filamentous fungi and yeasts such as acetamidase genes or cDNAs (the amdS, niaD, facA genes or cDNAs from *A. nidulans, A. oryzae,* or *A. niger*), or genes providing resistance to antbiotics like G418, hygromycin, bleomycin, kanamycin, phleomycin or benomyl resistance (benA). Alternatively, specific selection markers can be used such as auxotrophic markers which require corresponding mutant host strains: e.g. URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

Other markers include ATP synthetase subunit 9 (oliC), orotidine-5'-phosphate-decarboxylase (pvrA), the bacterial G418 resistance gene (useful in yeast, but not in filamentous fungi), the ampicillin resistance gene (*E. coli*), the neomycin resistance gene (*Bacillus*) and the *E. coli* uidA gene, coding for glucuronidase (GUS). Vectors may be used in vitro, for example for the production of RNA or to transfect or transform a host cell.

For most filamentous fungi and yeast, the expression construct is preferably integrated into the genome of the host cell in order to obtain stable transformants. However, for certain yeasts suitable episomal vector systems are also available into which the expression construct can be incorporated for stable and high level expression. Examples thereof include vectors derived from the 2 μm, CEN and pKD1 plasmids of *Saccharomyces* and *Kluyveromyces*, respectively, or vectors containing an AMA sequence (e.g. AMA1 from *Aspergillus*). When expression constructs are integrated into host cell genomes, the constructs are either integrated at random loci in the genome, or at predetermined target loci using homologous recombination, in which case the target loci preferably comprise a highly expressed gene. A highly expressed gene is a gene whose mRNA can make up at least 0.01% (w/w) of the total cellular mRNA, for example under induced conditions, or alternatively, a gene whose gene product can make up at least 0.2% (w/w) of the total cellular protein, or, in case of a secreted gene product, can be secreted to a level of at least 0.05 g/l.

An expression construct for a given host cell will usually contain the following elements operably linked to each other in consecutive order from the 5'-end to 3'-end relative to the coding strand of the sequence encoding the polypeptide of the first aspect: (1) a promoter sequence capable of directing transcription of the DNA sequence encoding the polypeptide in the given host cell, (2) preferably, a 5'-untranslated region (leader), (3) optionally, a signal sequence capable of directing secretion of the polypeptide from the given host cell into the culture medium, (4) the DNA sequence encoding a mature and preferably active form of the polypeptide, and preferably also (5) a transcription termination region (terminator) capable of terminating transcription downstream of the DNA sequence encoding the polypeptide.

Downstream of the DNA sequence encoding the polypeptide, the expression construct preferably contains a 3' untranslated region containing one or more transcription termination sites, also referred to as a terminator. The origin of the terminator is less critical. The terminator can for example be native to the DNA sequence encoding the polypeptide. However, preferably a yeast terminator is used in yeast host cells and a filamentous fungal terminator is used in filamentous fungal host cells. More preferably, the terminator is endogenous to the host cell in which the DNA sequence encoding the polypeptide is expressed.

Enhanced expression of the polynucleotide encoding the polypeptide of the invention may also be achieved by the selection of heterologous regulatory regions, e.g. promoter, signal sequence and terminator regions, which serve to increase expression and, if desired, secretion levels of the protein of interest from the chosen expression host and/or to provide for the inducible control of the expression of the polypeptide of the invention.

Aside from the promoter native to the gene encoding the polypeptide of the invention, other promoters may be used to direct expression of the polypeptide of the invention. The promoter may be selected for its efficiency in directing the expression of the polypeptide of the invention in the desired expression host.

Promoters/enhancers and other expression regulation signals may be selected to be compatible with the host cell for which the expression vector is designed. For example prokaryotic promoters may be used, in particular those suitable for use in *E. coli* strains. When expression of the polypeptides of the invention is carried out in mammalian cells, mammalian promoters may be used. Tissues-specific promoters, for example hepatocyte cell-specific promoters, may also be used. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, herpes simplex virus promoters or adenovirus promoters.

Suitable yeast promoters include the *S. cerevisiae* GAL4 and ADH promoters and the *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

Mammalian promoters, such as β-actin promoters, may be used. Tissue-specific promoters, in particular endothelial or neuronal cell specific promoters (for example the DDAHI and DDAHII promoters), are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

A variety of promoters can be used that are capable of directing transcription in the host cells of the invention. Preferably the promoter sequence is derived from a highly expressed gene as previously defined. Examples of preferred highly expressed genes from which promoters are preferably derived and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK), alcohol dehydrogenases (ADH), as well as genes encoding amylases, glucoamylases, proteases, xylanases, cellobiohydrolases, β-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Examples of strong constitutive and/or inducible promoters which are preferred for use in fungal expression hosts are those which are obtainable from the fungal genes for xylanase (xlnA), phytase, ATP synthetase subunit 9 (oliC) triose phosphate isomerase (tpi), alcohol dehydrogenase (AdhA), amylase (amy), amyloglucosidase (AG from the glaA gene), acetamidase (amdS) and glyceraldehyde-3-phosphate dehydrogenase (gpd) promoters.

Examples of strong yeast promoters which may be used include those obtainable from the genes for alcohol dehydrogenase, lactase, 3-phosphoglycerate kinase and triosephosphate isomerase.

Examples of strong bacterial promoters which may be used include the amylase and SPo2 promoters as well as promoters from extracellular protease genes.

Promoters suitable for plant cells which may be used include napaline synthase (nos), octopine synthase (ocs), mannopine synthase (mas), ribulose small subunit (rubisco ssu), histone, rice actin, phaseolin, cauliflower mosaic virus (CMV) 35S and 19S and circovirus promoters.

The vector may further include sequences flanking the polynucleotide giving rise to RNA which comprise sequences homologous to ones from eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses (such as HPV-16 or HPV-18). Gene transfer techniques using these viruses are known to those skilled in the art. Retrovirus vectors for example may be used to stably integrate the polynucleotide giving rise to the antisense RNA into the host genome. Replication-defective adenovirus vectors by contrast remain episomal and therefore allow transient expression.

The vector may contain a polynucleotide of the invention oriented in an antisense direction to provide for the production of antisense RNA. This may be used to reduce, if desirable, the levels of expression of the polypeptide.

Host Cells and Expression

In a further aspect the invention provides a process for preparing a polypeptide of the invention which comprises cultivating a host cell transformed or transfected with an expression vector as described above under conditions suitable for expression by the vector of a coding sequence encoding the polypeptide, and recovering the expressed polypeptide. Polynucleotides of the invention can be incorporated into a recombinant replicable vector, such as an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell. Suitable host cells include bacteria such as *E coli*, yeast, mammalian cell lines and other eukaryotic cell lines, for example insect cells such as Sf9 cells and (e.g. filamentous) fungal cells.

Preferably the polypeptide is produced as a secreted protein in which case the DNA sequence encoding a mature form of the polypeptide in the expression construct is operably linked to a DNA sequence encoding a signal sequence. In the case where the gene encoding the secreted protein has in the wild type strain a signal sequence preferably the signal sequence used will be native (homologous) to the DNA sequence encoding the polypeptide. Alternatively the signal sequence is foreign (heterologous) to the DNA sequence encoding the polypeptide, in which case the signal sequence is preferably endogenous to the host cell in which the DNA sequence is expressed. Examples of suitable signal sequences for yeast host cells are the signal sequences derived from yeast MFalpha genes. Similarly, a suitable signal sequence for filamentous fungal host cells is e.g. a signal sequence derived from a filamentous fungal amyloglucosidase (AG) gene, e.g. the *A. niger* glaA gene. This signal sequence may be used in combination with the amyloglucosidase (also called (gluco)amylase) promoter itself, as well as in combination with other promoters. Hybrid signal sequences may also be used within the context of the present invention.

Preferred heterologous secretion leader sequences are those originating from the fungal amyloglucosidase (AG) gene (glaA—both 18 and 24 amino acid versions e.g. from *Aspergillus*), the MFalpha gene (yeasts e.g. *Saccharomyces* and *Kluyveromyces*) or the alpha-amylase gene (*Bacillus*).

The vectors may be transformed or transfected into a suitable host cell as described above to provide for expression of a polypeptide of the invention. This process may comprise culturing a host cell transformed with an expression vector as described above under conditions suitable for expression of the polypeptide, and optionally recovering the expressed polypeptide.

A further aspect of the invention thus provides host cells transformed or transfected with or comprising a polynucleotide or vector of the invention. Preferably the polynucleotide is carried in a vector which allows the replication and expression of the polynucleotide. The cells will be chosen to be compatible with the said vector and may for example be prokaryotic (for example bacterial), or eukaryotic fungal, yeast or plant cells.

The invention encompasses processes for the production of a polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is herein defined as a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over filamentous fungal cells because they are easier to manipulate. However, some proteins are either poorly secreted from yeasts, or in some cases are not processed properly (e.g. hyperglycosylation in yeast). In these instances, a filamentous fungal host organism should be selected.

Bacteria from the genus *Bacillus* are very suitable as heterologous hosts because of their capability to secrete proteins into the culture medium. Other bacteria suitable as hosts are those from the genera *Streptomyces* and *Pseudomonas*. A preferred yeast host cell for the expression of the DNA sequence encoding the polypeptide is one of the genus *Saccharomyces, Kluyveromyces, Hansenula, Pichia, Yarrowia*, or *Schizosaccharomyces*. More preferably, a yeast host cell is selected from the group consisting of the species *Saccharomyces cerevisiae, Kluyveromyces lactis* (also known as *Kluyveromyces* marxianus var. *lactis*), *Hansenula polymorpha, Pichia pastoris, Yarrowia lipolytica*, and *Schizosaccharomyces pombe*.

Most preferred for the expression of the DNA sequence encoding the polypeptide are, however, filamentous fungal host cells. Preferred filamentous fungal host cells are selected from the group consisting of the genera *Aspergillus, Trichoderma, Fusarium, Disporotrichum, Penicillium, Acremonium, Neurospora, Thermoascus, Myceliophtora, Sporotrichum, Thielavia*, and *Talaromyces*. More preferably a filamentous fungal host cell is of the species *Aspergillus oyzae, Aspergillus sojae* or *Aspergillus nidulans* or is of a species from the *Aspergillus niger* Group (as defined by Raper and Fennell, The Genus *Aspergillus*, The Williams & Wilkins Company, Baltimore, pp 293-344, 1965). These include but are not limited to *Aspergillus niger, Aspergillus awamori, Aspergillus tubigensis, Aspergillus aculeatus, Aspergillus foetidus, Aspergillus nidulans, Aspergillus japonicus, Aspergillus oryzae* and *Aspergillus ficuum*, and also those of the species *Trichoderma reesei, Fusarium graminearum, Penicillium chrysogenum, Acremonium alabamense, Neurospora crassa, Myceliophtora thermophilum, Sporotrichum cellulophilum, Disporotrichum dimorphosporum* and *Thielavia terrestris*.

Examples of preferred expression hosts within the scope of the present invention are fungi such as *Aspergillus* species (in particular those described in EPA-184,438 and EP-A-284,603) and *Trichoderma* species; bacteria such as *Bacillus* species (in particular those described in EP-A-134,048 and EP-A-253,455), especially *Bacillus subtilis, Bacillus licheniformis, Bacillus amyloliquefaciens, Pseudomonas* species; and yeasts such as *Kluyveromyces* species (in particular those described in EP-A-096,430 such as *Kluyveromyces lactis* and in EP-A-301,670) and *Saccharomyces* species, such as *Saccharomyces cerevisiae*.

Host cells according to the invention include plant cells, and the invention therefore extends to transgenic organisms, such as plants and parts thereof, which contain one or more cells of the invention. The cells may heterologously express the polypeptide of the invention or may heterologously contain one or more of the polynucleotides of the invention. The transgenic (or genetically modified) plant may therefore have inserted (typically stably) into its genome a sequence encoding the polypeptides of the invention. The transformation of plant cells can be performed using known techniques, for example using a Ti or a Ri plasmid from *Agrobacterium tumefaciens*. The plasmid (or vector) may thus contain sequences necessary to infect a plant, and derivatives of the Ti and/or Ri plasmids may be employed.

The host cell may overexpress the polypeptide, and techniques for engineering over-expression are well known and can be used in the present invention. The host may thus have two or more copies of the polynucleotide.

Alternatively, direct infection of a part of a plant, such as a leaf, root or stem can be effected. In this technique the plant to be infected can be wounded, for example by cutting the plant with a razor, puncturing the plant with a needle or rubbing the plant with an abrasive. The wound is then innoculated with the *Agrobacterium*. The plant or plant part can then be grown on a suitable culture medium and allowed to develop into a mature plant. Regeneration of transformed cells into genetically modified plants can be achieved by using known techniques, for example by selecting transformed shoots using an antibiotic and by sub-culturing the shoots on a medium containing the appropriate nutrients, plant hormones and the like.

Culture of Host Cells and Recombinant Production

The invention also includes cells that have been modified to express the proline specific endoprotease or a variant thereof. Such cells include transient, or preferably stably modified higher eukaryotic cell lines, such as mammalian cells or insect cells, lower eukaryotic cells, such as yeast and filamentous fungal cells or prokaryotic cells such as bacterial cells.

It is also possible for the polypeptides of the invention to be transiently expressed in a cell line or on a membrane, such as for example in a baculovirus expression system. Such systems, which are adapted to express the proteins according to the invention, are also included within the scope of the present invention.

According to the present invention, the production of the polypeptide of the invention can be effected by the culturing of microbial expression hosts, which have been transformed with one or more polynucleotides of the present invention, in a conventional nutrient fermentation medium.

The recombinant host cells according to the invention may be cultured using procedures known in the art. For each combination of a promoter and a host cell, culture conditions are available which are conducive to the expression the DNA sequence encoding the polypeptide. After reaching the desired cell density or titre of the polypeptide the culturing is ceased and the polypeptide is recovered using known procedures.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (dependent on the expression construct used) may be included or subsequently be added.

The selection of the appropriate medium may be based on the choice of expression host and/or based on the regulatory requirements of the expression construct. Suitable media are well-known to those skilled in the art. The medium may, if desired, contain additional components favoring the transformed expression hosts over other potentially contaminating microorganisms.

The fermentation may be performed over a period of from 0.5-30 days. Fermentation may be a batch, continuous or fed-batch process, at a suitable temperature in the range of between 0° C. and 45° C. and, for example, at a pH from 2 to 10. Preferred fermentation conditions include a temperature in the range of between 20° C. and 37° C. and/or a pH between 3 and 9. The appropriate conditions are usually selected based on the choice of the expression host and the protein to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means. The proline specific endoprotease of the invention can be purified from fungal mycelium or from the culture broth into which the proline specific endoprotease is released by the cultured fungal cells.

In a preferred embodiment the polypeptide is obtained from a fungus, more preferably from an *Aspergillus*, most preferably from *Aspergillus niger*.

Modifications

Polypeptides of the invention may be chemically modified, e.g. post-translationally modified. For example, they may be glycosylated (one or more times) or comprise modified amino acid residues. They may also be modified by the addition of histidine residues to assist their purification or by the addition of a signal sequence to promote secretion from the cell. The polypeptide may have amino- or carboxyl-terminal extensions, such as an amino-terminal methionine residue, a small linker peptide of up to about 20-25 residues, or a small extension that facilitates purification, such as a poly-histidine tract, an antigenic epitope or a binding domain.

A polypeptide of the invention may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin.

The polypeptides may be modified to include non-naturally occurring amino acids or to increase the stability of the polypeptide. When the proteins or peptides are produced by synthetic means, such amino acids may be introduced during production. The proteins or peptides may also be modified following either synthetic or recombinant production.

The polypeptides of the invention may also be produced using D-amino acids. In such cases the amino acids will be linked in reverse sequence in the C to N orientation. This is conventional in the art for producing such proteins or peptides.

A number of side chain modifications are known in the art and may be made to the side chains of the proteins or peptides of the present invention. Such modifications include, for example, modifications of amino acids by reductive alkylation by reaction with an aldehyde followed by reduction with NaBH$_4$, amidination with methylacetimidate or acylation with acetic anhydride.

The sequences provided by the present invention may also be used as starting materials for the construction of "second generation" enzymes. "Second generation" proline specific proteases are proline specific proteases, altered by mutagenesis techniques (e.g. site-directed mutagenesis), which have properties that differ from those of wild-type proline specific protease or recombinant proline specific proteases such as those produced by the present invention. For example, their temperature or pH optimum, specific activity, substrate affinity or thermostability may be altered so as to be better suited for use in a particular process.

Amino acids essential to the activity of the proline specific protease of the invention, and therefore preferably subject to substitution, may be identified according to procedures known in the art, such as site-directed mutagenesis or alanine-scanning mutagenesis. In the latter technique mutations are introduced at every residue in the molecule, and the resultant mutant molecules are tested for biological activity (e.g. proline specific endoprotease activity) to identify amino acid residues that are critical to the activity of the molecule. Sites of enzyme-substrate interaction can also be determined by analysis of crystal structure as determined by such techniques as nuclear magnetic resonance, crystallography or photo-affinity labelling.

The use of yeast and filamentous fungal host cells is expected to provide for such post-translational modifications (e.g. proteolytic processing, myristilation, glycosylation, truncation, and tyrosine, serine or threonine phosphorylation) as may be needed to confer optimal biological activity on recombinant expression products of the invention.

Preparations

Polypeptides of the invention may be in an isolated form. It will be understood that the polypeptide may be mixed with carriers or diluents which will not interfere with the intended purpose of the polypeptide and still be regarded as isolated. A polypeptide of the invention may also be in a substantially purified form, in which case it will generally comprise the polypeptide in a preparation in which more than 70%, e.g. more than 80%, 90%, 95%, 98% or 99% of the proteins in the preparation is a polypeptide of the invention.

Polypeptides of the invention may be provided in a form such that they are outside their natural cellular environment. Thus, they may be substantially isolated or purified, as discussed above, or in a cell in which they do not occur in nature, for example a cell of other fungal species, animals, plants or bacteria.

Removal or Reduction of Proline Specific Endoprotease Activity

The present invention also relates to methods for producing a mutant cell of a parent cell, which comprises disrupting or deleting the endogenous nucleic acid sequence encoding the polypeptide or a control sequence thereof, which results in the mutant cell producing less of the polypeptide than the parent cell.

The construction of strains which have reduced proline specific endoprotease activity may be conveniently accomplished by modification or inactivation of a nucleic acid sequence necessary for expression of the proline specific endoprotease in the cell. The nucleic acid sequence to be modified or inactivated may be, for example, a nucleic acid sequence encoding the polypeptide or a part thereof essential for exhibiting proline specific endoprotease activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification include, but are not limited to, a leader sequence, a polyadenylation sequence, a propeptide sequence, a signal sequence, and a termination sequence.

Modification or inactivation of the nucleic acid sequence may be performed by subjecting the cell to mutagenesis and selecting cells in which the proline specific endoprotease producing capability has been reduced or eliminated. The mutagenesis, which may be specific or random, may be performed, for example, by use of a suitable physical or chemical mutagenizing agent, by use of a suitable oligonucleotide, or by subjecting the DNA sequence to PCR mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotde analogues.

When such agents are used, the mutagenesis is typically performed by incubating the cell to be mutagenized in the presence of the mutagenizing agent of choice under suitable conditions, and selecting for cells exhibiting reduced or no expression of proline specific endoprotease activity.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR mutagenesis in accordance with methods known in the art.

Although, in principle, the modification may be performed in vivo, i.e., directly on the cell expressing the nucleic acid sequence to be modified, it is preferred that the modification be performed in vitro as exemplified below.

An example of a convenient way to inactivate or reduce production of the proline specific endoprotease by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. Preferably the defective gene or gene fragment also encodes a marker which may be used to select for transformants in which the gene encoding the polypeptide has been modified or destroyed.

Alternatively, modification or inactivation of the nucleic acid sequence encoding a polypeptide of the present invention may be achieved by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide. The antisense polynucleotide will then typically be transcribed in the cell and will be capable of hybridizing to the mRNA encoding the proline specific endoprotease. Under conditions allowing the complementary antisense nucleotide sequence to hybridize to the mRNA, the amount of the proline specific endoprotease produced in the cell will be reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of the endogenous nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) culturing the mutant cell under conditions conducive for production of the polypeptide; and (b) recovering the polypeptide. In the present context, the term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a still further aspect, the present invention provides a method for producing a protein product essentially free of proline specific endoprotease activity by fermentation of a cell which produces both an proline specific endoprotease polypeptide of the present invention as well as the protein product of interest. The method comprises adding an effective amount of an agent capable of inhibiting proline specific endoprotease activity to the fermentation broth either during or after the fermentation has been completed, recovering the product of interest from the fermentation broth, and optionally subjecting the recovered product to further purification. Alternatively, after cultivation the resultant culture broth can be subjected to a pH or temperature treatment so as to reduce the proline specific endoprotease activity substantially, and allow recovery of the product from the culture broth. The combined pH or temperature treatment may be performed on an protein preparation recovered from the culture broth.

The methods of the present invention for producing an essentially proline specific endoprotease-free product is of particular interest in the production of eukaryotic polypeptides, in particular in the production of fungal proteins such as enzymes. The proline specific endoprotease-deficient cells may also be used to express heterologous proteins of interest for the food industry, or of pharmaceutical interest.

Preferred sources for the proline-specific endoprotease are obtained by cloning a microbial gene encoding a proline-specific endoprotease into a microbial host organism. More preferred sources for the proline-specific endoprotease are obtained by cloning an *Aspergillus*-derived gene encoding a proline-specific endoprotease into a host belonging to the genus of *Aspergillus* capable of overexpressing the proline-specific endoprotease gene.

In the category of products containing protein hydrolysates targeting consumers with non-medical needs, the niche market of employing protein hydrolysates in products for athletes is rapidly increasing. In this product category, the allergenicity of the final product is not an issue. Instead, aspects such as taste, nutritional value and the presence of specific amino acids to support endurance and stimulate physiological recovery after exercise are important parameters for such hydrolysates, particularly when used in sport drinks. For example, glutamine has been implicated in fighting metabolic stresses but can only be supplied in small peptides, as the free amino acid is not stable in solution. Protein hydrolysates produced according to the invention are very suitable for use in athletic-related products due to their very high solubility under the acid pH conditions prevalent, for example, in sport drinks. An important implication of this criterion is that high levels of hydrolysates produced according to the invention can be included in nutritional sport products without the drawback of protein precipitation upon sterilisation and prolonged storage. Thus, the shelf lives of sport products may be extended by the addition of a protein hydrolysate of the invention.

The enzyme mixture according to the invention may be used to hydrolyze proteinaceous materials of animal origin such as whole milk, skim milk, casein, whey protein or mixtures of casein and whey protein. Such mixtures of casein and whey protein may be used, for example, in ratios similar to those found in human milk. Furthermore, collagen based animal proteins forms a substrate because of the possibility to degrade these proteins to smaller molecules hereby debittering animal meat extracts or improving the uptake of proline and hydroxyproline residues with benefits on the joints of athletes.

The enzyme mixture according to the invention may also be used to hydrolyze proteinaceous materials of plant origin such as, for example, wheat gluten malted or unmalted barley or other cereals used for making beer, soy milk, concentrates or isolates thereof, maize protein concentrates and isolates thereof, and rice proteins.

The invention will be further illustrated by the following non-limiting Examples.

EXAMPLES

Materials and Methods

Beta-casein from bovine milk (lyophilised, essentially salt-free powder) with a minimum 90% beta-casein was obtained from Sigma. Collagen (Type 1, insoluble from bovine achilles tendon) was also obtained from Sigma.

Sodium caseinate (MIPRODAN 30®) was obtained from MD Foods (Viby, Denmark). Sweet whey concentrate, non-pasteurised, 10% ds, 35% protein was obtained from Borculo Domo (Zwolle, The Netherlands).

A low bitterness whey hydrolysate VITALARMOR® 800 LB as well as whey protein enriched in beta-lactoglobulin (PROTARMOR® 905) was obtained from Armor Proteines (Saint-Brice-en-Cogles, France). Other commercial hydrolysates were obtained from the producer or purchased in pharmacies.

Soy isolate was obtained as SOYAMIN®90 HV from Lucas Meyer, Hamburg, Germany.

Subtilisin from B. licheniformis (DELVOLASE®, 560 000 DU per gram) was obtained from DSM Food Specialities (Seclin, France). SUMIZYME® LP 75.000 was obtained from Shin Nihon (Anjyo, Japan). FLAVOURZYME® 1000 L was obtained from NOVO Industries, Bagsvaerd, Denmark. Thermolysin (THERMOASE; a heat stable metallo-endoprotease from Bacillus thermoproteolyticus Rokko with an activity of 14000 PU/mg as produced by Daiwa Kasei, Osaka, Japan).

Proline-specific endoprotease from Flavobacterium meningosepticum and cloned in E. coli was isolated using known plasmid constructs and enzyme purification methods (T. Diefenthal and H. Dargatz, World Journal of Microbiology &Biotechnology 11, 209-212 (1995)) The enzymatic activity was tested on CBZ-Gly-Pro-pNA 0.26 mM in phosphate buffer 0.1 M pH 7.0 at 25° C. pH 7.0 was used in this test because the pH optimum of this enzyme is above pH 6.0. The product was monitored spectrophotometricallyat 410 nm.

A unit was defined as the quantity of enzyme that provokes the release of 1 µmol of p-nitroanilide per minute under these conditions.

Proline specific endoproteases from Aspergill were measured according to the method described in Japanese patent JP5015314 with minor modifications. In brief the enzymatic activity is tested on CBZ-Gly-Pro-pNA at 37 degrees C. in a citrate/disodium phosphate buffer pH 5. pH 5.0 is chosen because in this test the pH optimum of the enzyme is below pH 6. The reaction product was also monitored spectrophotometrically at 410 nM.

Two-Dimensional Gelelectrophoresis

Two-dimensional gelelectrophoresis and partial amino acid sequencing of a proline-specific endopeptidase from Aspergillus niger.

Proline-specific endoprotease from A. niger G-306 was produced and isolated as outlined in Example 4. Complete purification was realised using two-dimensional gel electrophoresis. To that end the active material isolated from the SUPERDEX 75 column was first desalted by dilution (approx 20 fold) in 10 mM Tris/HCl buffer pH 6.8 and then concentrated with a Centricon 30 kD miniconcentrator (Amicon).

Basically the two-dimensional electrophoresis was performed as described in "2-D electrophoresis using immobilized pH gradients; Principles and Methods; Amersham Pharmacia Biotech 80-6429-60 Rev A/10-98". The first dimension (IEF) was performed on an IPGphor (Amersharm-Pharmacia) using a 11 cm IPG strip pH range 3-6 (BioRad) The desalted, 3-fold concentrated sample was diluted in 8M urea (6M urea and 2M thiourea) This was mixed with 18.5 microliters of 10X-concentrated rehydration buffer, containing 6M urea, 2M thiourea 20% CHAPS, and 5% IPG buffer range 3-10. The total was used to rehydrate the IPG strip. Focussing was done during 29.320 Vh using the protocol as described in the Biorad leaflet supplied with the strips as a guideline.

The second dimension (SDS) was done on a Criterion Mini Vertical Cell (BioRad) using a precast gel of 12% (Type Prep+2 Comb) purchased from BioRad.

The IPG strip was first incubated in SDS equilibration buffer containing DTT (1%) and a second time in buffer containing Iodoacetamide (2.5%) Both incubations were for 15 minutes at 20° C. The SDS equilibration buffer consisted of Tris/HCl 50 mM pH 8.8, 6M urea, 30% (v/v) glycerol and 2% (w/v) SDS and a trace of bromophenol blue.

After incubation the IPG strip was trimmed to fit the gel type mentioned and ran with 10× diluted TGS buffer (Bio-Rad). After the run the gel was stained with Sypro Ruby (Molecular Probes, Leiden, The Netherlands) for 3-4 hours and washed with Milli Q water for 2 hours. Imaging was performed on The Imager (Appligene). The largest spot was cut out, washed several times with 50 millimoles/litre ammonium bicarbonate, incubated overnight at 37 degrees C. with sequencing grade trypsin (nr.1047841, Boehringer Mannheim). Peptides were extracted from the gel piece by washing several times with acetonitrile/water containing formic acid (50/50/5, v/v/v). The samples were dried using a vacuum centrifuge (New Brunswick Scientific, The Netherlands) and stored at −20° C. until analysis.

LC/MS Analysis

HPLC (high performance liquid chromatography) using a Qtof-2 (Micromass, Manchester, UK) mass spectrometer was used to separate the peptides formed during digestion with trypsin. 5 microliter of the peptide solution was trapped on a micro-precolumn, C18, 5*0.3 mm (MCA30-05-C18, LC Packings, Amsterdam, Netherlands) using Milli Q water containing 0.1% of formic acid at a flow-rate of 20 microliter/min. The peptides were then eluted from the precolumn, using a fast gradient of 0.1% formic acid in Milli Q water (Millipore, Bedford, Mass., USA; Solution A) and 0.1% formic acid in acetonitrile (Solution B). The gradient started at 100% of Solution A and increased to 60% of solution B in 20 minutes and was kept at the latter ratio for another 5 minutes. The flow rate used during elution of the peptides was 200 nl/min. Using LC/MS/MS analysis partial amino acid sequences of the *A. niger* proline-specific endopeptidase could be determined, by de novo sequencing of suitable peptides.

HPLC using an ion trap mass spectrometer (THERMOQUES™, Breda, the Netherlands) coupled to a P4000 pump (THERMOQUEST™, Breda, the Netherlands) was used in characterising the enzymatic protein hydrolysates produced by the inventive enzyme mixture. The peptides formed were separated using a PEPMAP C18 300A (MIC-15-03-C18-PM, LC Packings, Amsterdam, The Netherlands) column in combination with a gradient of 0.1% formic acid in Milli Q water (Millipore, Bedford, Mass., USA; Solution A) and 0.1% formic acid In acetonitrile (Solution B) for elution. The gradient started at 100% of Solution A and increased to 70% of solution B in 45 minutes and was kept at the latter ratio for another 5 minutes. The injection volume used was 50 microliters, the flow rate was 50 microliter per minute and the column temperature was maintained at 30° C. The protein concentration of the injected sample was approx. 50 micrograms/milliliter.

Detailed information on the individual peptides was obtained by using the "scan dependent" MS/MS algorithm which is a characteristic algorithm for an ion trap mass spectrometer.

Full scan analysis was followed by zoom scan analysis for the determination of the charge state of the most intense ion in the full scan mass range. Subsequent MS/MS analysis of the latter ion resulted in partial peptide sequence information, which could be used for database searching using the SEQUEST application from Xcalibur Bioworks (THERMOQUEST™, Breda, The Netherlands). Databanks used were extracted from the OWL.fasta databank, available at the NCBI (National Centre for Biotechnology informatics), containing the proteins of interest for the application used. In those experiments in which well characterized protein substrates such as whey proteins or caseins were measured, the precision of the analysis technique was increased by omitting those MS/MS spectra with a sequence fit of less than 50%.

Only peptides with a mass ranging from approx. 400 to 2000 Daltons were considered suitable for further analysis by MS sequencing. Angiotensin (M=1295.6) was used to tune for optimal sensitivity in MS mode and for optimal fragmentation in MS/MS mode, performing constant infusion of 60 µg/ml, resulting in mainly doubly and triply charged species in MS mode, and an optimal collision energy of about 35% in MS/MS mode.

LC/MS Analysis of Infant Formulae and Commercial Protein Hydrolysates.

Prior to LC/MS fatty material had to be removed from the infant formulae. To that end the complete nutrition samples (13.5 g powder in 100 ml MilliQ water) were extracted 3 times with 30 ml hexane. Small amounts of NaCl were added to improve separation of the solvent layers. Then 5 ml of the water layer was obtained and freeze dried. Prior to analysis the sample was redissolved in 25 ml of MilliQ water, centrifugated 2 times (at 13000 rpm) and filtered through a 0.22 µm filter. From pure hydrolysated samples, 400 mg was dissolved in 100 ml MilliQ water, centrifugated 2 times (at 13000 rpm) and filtered through a 0.22 µm filter. To characterise the peptides present in the commercial protein hydrolysates, the same strategy was followed as described above for the enzymatic hydrolysates formed by the inventive enzyme mixture i.e. the filtered hydrolysate was applied to the HPLC column and Individual peptides with molecular masses between 400 and 2000 daltons were further characterised by the MS/MS analysis. However, the databank used to obtain peptide sequence information on whey or casein derived hydrolysates consisted of cow milk protein sequences only.

Determination of the molar fraction of Peptides (%) Carrying a Carboxyterminal Proline.

LC/MS/MS can be used for the analysis of the C-terminus of a peptide. With an algorithm in which the peptide's molecular mass (analyzed with LC/MS) and its (partial) amino acid sequence (analyzed with LC/MS/MS) are linked with automatic search procedures within protein databanks, complex peptide mixtures can be analyzed. These options have enabled us to quantify the incidence of peptides carrying a carboxy terminal proline residue. Owing to the limitations set by the PEPMAP peptide separation column used, only peptides with a molecular weight between roughly 400 and 2000 Dalton are analysed using this technique. Fortunately, in protein hydrolysates the majority of the peptides have such molecular weights.

To determine in a protein hydrolysate the molar fraction of peptides carrying a carboxyterminal proline, individual peptide peaks eluting from the PEPMAP column are selected and partial carboxyterminal amino acid sequences are determined using the techniques specified above. Analysis of at least 20, preferably at least 30 and more preferably between 40 to 60, for example 50 of the most abundant, randomly choosen peptides thus provides insight in the frequency in which peptides carrying a proline residue at the carboxyterminus of the peptide occur. The quotient of the number of peptides found to carry a carboxyterminal proline residue times 100 and the total number of peptides analysed thus provides the molar fraction of peptides (%) carrying a carboxyterminal proline.

Determination of the Molar Fraction (%) of Proline in the Protein Substrate Used to Generate the Hydrolysate.

Fatty material as can occur in infant formulae products was first removed by hexane extraction as detailed in the paragraph describing LC/MS analysis of infant formulae and commercial protein hydrolysates. Acid hydrolysis of the protein substrate to convert the proteins present into free amino acids, was achieved by making a suspension of 100 milligrams of proteinaceous material in 2 milliliters 6 N HCl. Acid hydrolysis was carried out for 22 hours at 112 degrees C. in an oxygen free atmosphere. After centrifugation the supernatant was diluted 10 times in dilute HCl. After this hydrolysis the amino acids were derivatised and analysed according to the Picotag method as specified in the operators manual of the Amino Acid Analysis System of Waters (Milford Mass., USA). The level of proline present was quantitated using HPLC methods. To determine the molar fraction (%) of proline in the sample, the micromoles of proline present times 100 were divided by the sum of the micromoles of all amino acids present in the sample analysed. Since during acid hydrolysis Trp and Cys are destroyed, these two amino acids are not included in this sum of the micromoles of all amino acids.

Determination of the Free Amino Acid Levels in Protein Hydrolysates or Infant Formulae.

A precisely weighed sample of the proteinaceous material was dissolved in dilute acid and precipitates were removed by centrifugation in an Eppendorf centrifuge. Amino acid analysis was carried out on the clear supernatant according to the PicoTag method as specified in the operators manual of the Amino Acid Analysis System of Waters (Milford Mass., USA). To that end a suitable sample was obtained from the liquid, added to dilute acid and homogenized. From the latter solution a new sample was taken, dried and derivatised using phenylisothiocyanate. The various derivatised amino acids present were quantitated using HPLC methods and added up to calculate the total level of free amino acids in the weighed sample.

To relate this total level of free amino acids in the sample to the total level of amino acids that can be liberated from this sample, the sample is also subjected to add hydrolysis followed by a quantification of the total free amino acids present as detailed above.

LEGENDS TO THE FIGURES

FIG. 1: Plasmid map of expression plasmid pGBFIN11-EPO. Endo-Pro stands for the proline specific endoprotease.

Figure 2:
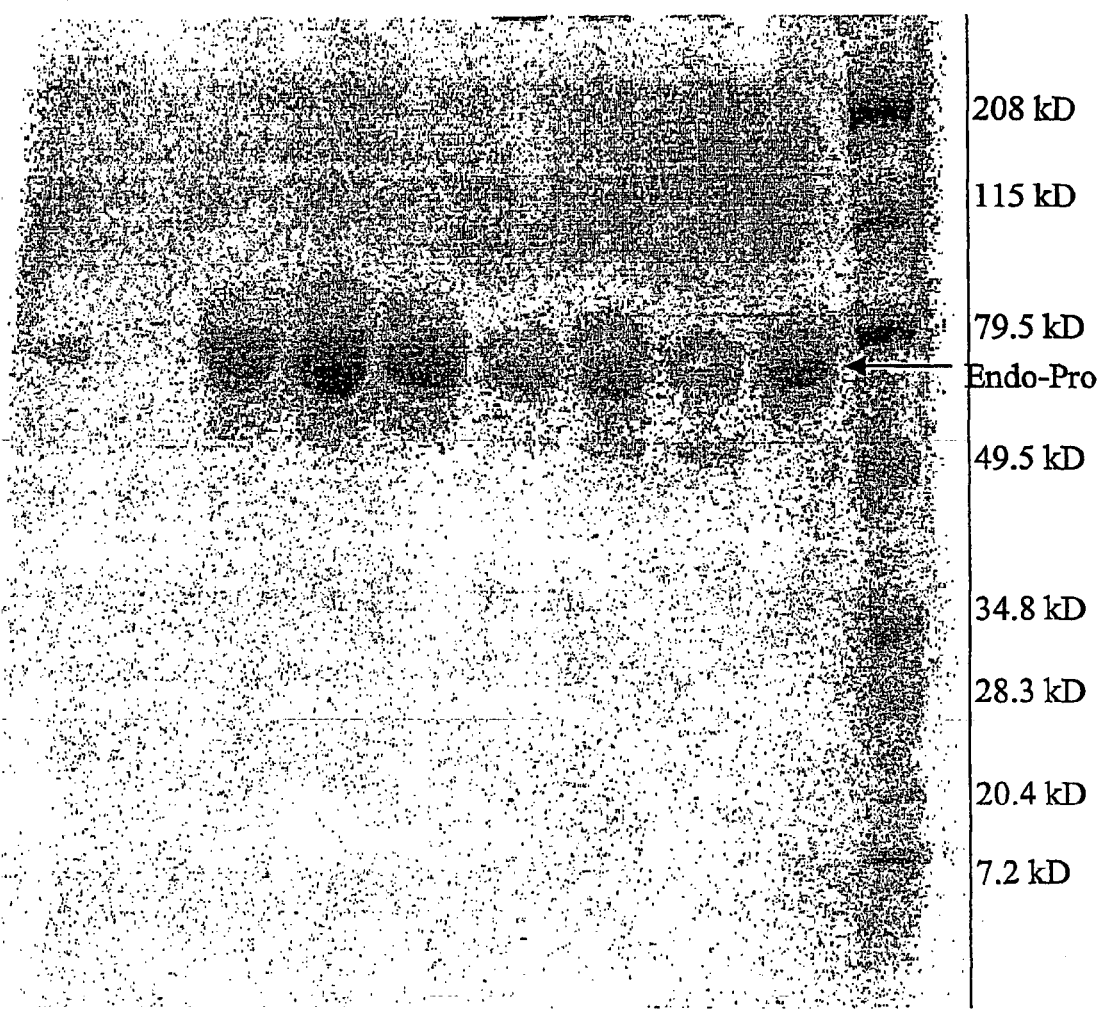
FIG. 2 shows SDS-PAGE analysis of culture filtrates of the host strain (*A. niger* CBS513.88) and several transformants (indicated by arrow) that over-express the proline specific endoprotease.

FIG. 2: SDS-PAGE analysis of culture filtrates of the host strain (*A. niger* CBS513.88) and several transformants that over-express the proline specific endoprotease, here indicated with the arrow.

EXAMPLE 1

Hydrolysis of Beta-Casein Using *Subtilisin* in Combination with a Proline Specific Endoprotease from *F. meningosepticum*.

Beta-casein represents one of the major casein fractions of bovine milk. The protein has been well characterised in terms of its amino acid sequence and is commercially available in an almost pure form. As such, beta-casein offers an excellent test substrate for studying the relationship between enzyme cleavage sites and the length of various peptides formed during enzyme hydrolysis.

This Example demonstrates that despite the broad spectrum character of *subtilisin*, the addition of a very specific enzyme like a proline-specific endoprotease can have a major impact on the size of the beta-casein fragments formed. Improved yields for casein fractions upon incubation with subtilisin in combination with a proline-specific endoprotease can therefore be obtained. Beta-casein is relatively rich in proline as acid hydrolysis followed by amino acid analysis carried out according to the Materials & Methods section revealed that its molar fraction of proline is 14% (moles of proline/moles of all amino acids as specified in the Materials & Methods section).

Beta-casein powder (Sigma) was dissolved at a concentration of 10% (w/w) together with 0.1% (w/w) DELVOLASE™ in a 0.1 mol/liter phosphate buffer pH7.0. After an incubation of 24 hours at 45° C. in a shaking waterbath, the reaction was stopped by heating the solution for 15 minutes at 90° C. To one half of the solution (1 ml containing 100 milligrams of beta-casein) 100 microliter of proline-specific endoprotease from *F. meningosepticum* (corresponding to 4 units according to the procedure described in World Journal of Microbiology & Biotechnology, Vol 11, pp 209-212) was added and the reaction was continued for another 24 hours at 45° C. After another heat shock at 90° C., samples of both the DELVOLASE™ and the DELVOLASE™+proline-specific endoprotease treated beta-casein material were analysed by LC/MS equipment as specified in the Materials and Methods section.

In the sample digested with DELVOLASE alone, the LC/MS/MS analysis identified 40 peptides covering various parts of the beta-casein molecule. Together these peptides accounted for 79% of the total beta-casein sequence. Different retention times of the peptides on the C18 column could be traced back to peptide lengths ranging from 2 to 23 amino acid residues. Glutamine proved to be the most frequently occurring carboxy terminal residue (10 out of 40 peptides). None of the peptides analysed could be shown to have proline as the carboxy terminal residue.

By contrast, the sample digested with DELVOLASE™ and proline-specific endoprotease generated 28 identifiable peptides from beta-casein. Together these peptides covered 63% of the total beta-casein protein sequence. Peptide size distribution was remarkably homogeneous, as the peptides ranged in length only between 3 and 9 residues. Within this peptide population, glutamine was the carboxy-terminal residue in 3 peptides only and proline proved to be the most abundant carboxy-terminal residue (in, 17 out of the 28 peptides analysed). The results show that in the hydrolysate made with the proline-specific endoprotease, those peptides that carry a carboxy terminal proline residue represent a molar fraction of 61% of the total of the peptides present in the molecular weight range between 400 and 2000 daltons. Thus, incubation of beta-casein with a proline-specific-endopeptidase results in the generation of peptides with proline as the carboxy terminal residue. Moreover, the combination of subtilisin plus a proline-specific endoprotease results in a remarkably homogeneous size distribution of the various peptides generated, suggesting high product yields upon ultrafiltration of such a hydrolysate.

EXAMPLE 2

Beta-casein hydrolysates and bitterness.

Although Example 1 Illustrates the effect of a proline-specific endoprotease on peptide size and the proportion of peptides with proline as the carboxy-terminal amino acid residue, the effect of this enzyme on bitterness was not measured in Example 1. Casein hydrolysates are notoriously bitter and this property has been linked to their relatively high content of hydrophobic amino acid residues.

To test the effect of a proline specific endoprotease on the taste of beta-casein hydrolyzed by a subtillsin, enzyme Incubations using DELVOLASE™ and the DELVOLASE™ with proline-specific endoprotease were performed as described in Example 1. Following heat inactivation of both subtilisin and proline-specific endoprotease, samples were cooled to room temperature and distilled water was added to give final casein concentrations of 4% (w/w). The taste of the latter solutions were then evaluated by a panel of experienced tasters. The tasters were unanimous in their conclusion that the hydrolysate obtained by the combination of subtilisin plus proline-specific endoprotease was significantly less bitter than the hydrolysate obtained using subtilisin alone.

Thus, the treatment of casein hydrolysates with a proline-specific endoprotease substancially reduces the bitterness of the final product.

EXAMPLE 3

Isolation of a Proline-Specific Endoprotease from *Aspergillus niger*.

A large collection of moulds capable of forming black spores were allowed to grow in a pH 6.5 medium containing 1.0 gram of K2HPO4, 0.5 gram of KH2PO4, 0.5 gram of KCl, 0.5 gram of MgSO4. 7H2O, 0.01 gram of FeSO4, 7H2O, 5 grams of glucose, 15 grams of collagen (Sigma) and distilled water added to obtain a volume of 1 litre. The inoculum for each experiment was prepared by a method in which the spores of fungi growing on an agar slant (5 days old) were taken up in 5 milliliters of sterile water. Of the later suspension, 2%(v/v) was used for inoculation of the pH 6.5 medium.

Growth was allowed for 100 hours at 28 degrees C. with shaking after which the culture was filtrated and samples of the clear filtrate were incubated with the synthetic peptide Z-Ala-Pro-pNA (Bachem; Bubendorf, Switzerland) at pH 5.0, 50 degrees C. Samples capable of releasing pNA were identified by measuring the increase in absorbance at 410 nanometer. Positive strains yielding relatively high activities were further investigated.

Strain G-306 excreted a proline-specific endoprotease and was identified as *Aspergillus niger* Van Tieghern var. *niger*. This particular strain was used for isolation, purification and further characterisation of a proline-specific endoprotease. To purify the enzyme 1 liter of culture supernatant was applied to a 400 milliliter bacitracin-silochrome column equilibrated with 0.05 mol/litre sodium acetate pH 5.0. Proteases bound to the column were eluted using the acetate buffer supplemented with 1 mol/itre of NaCl and 10% (v/v) isopropanol (J. Appl. Biochem.,1983 pp420-428). Active fractions were collected and dialysed against distilled water and applied on a 200 milliliter bacitracin-Sepharose column, again equilibrated with acetate buffer. As before, elution was carried out using the acetate buffer supplemented with NaCl and isopropanol. Active fractions were collected, dialysed against a 5 millimol/itre acetate buffer pH 5.0 and then concentrated by means of ultrafiltration with a Amicon PM-10 membrane. To obtain an almost completely pure proline-specific endoprotease, the concentrated liquid was chromatographed over a SUPERDEX™ 75 column eqiulibrated with the 0.05 mol/litre sodium acetate buffer pH 5.0 and supplemented with 0.5 mol/liter NaCl.

Further experiments carried out with the purified enzyme indicated a molecular weight around 66.6 kDalton, an IEP around pH 4.2, a pH optimum around 5.0 and an almost 100% thermostablity upon incubation for 4 hours at 50 degrees C.

To obtain partial amino acid sequences of the enzyme, the enzyme preparation isolated was first subjected to two-dimensional gel electrophoresis according to the procedure described in the Materials & Methods section. The largest spot was cut out, incubated with trypsin and eluted. The recovered peptides were then subjected to LC/MS/MS analysis as described in the Materials & Methods section to determine partial amino acid sequences.

The following amino acid sequences could be derived from the proline-specific endoprotease of *Aspergillus niger:*
NH2-ATTGEAYFE-COOH (SEQ ID NO: 3)
NH2-ATVNSWTGGWDFTR-COOH (SEQ ID NO: 6)
NH2-DGAPEGTST-COOH (SEQ ID NO: 9)
NH2-EREAGAAVTP-COOH (SEQ ID NO: 12).

These amino acid sequences were used to synthesize the DNA sequences needed for the isolation of the gene encoding the proline-specific endoprotease from *Aspergillus niger.*

In later experiments (see Example 10) the sequence NH2-ATTGEAYFE-COOH(SEQ ID NO: 3) could be shown to represent the amino terminus of the mature proline specific endoprotease.

EXAMPLE 4

Proline-specific endoprotease and its effects in the hydrolysis of soy protein.

Japanese patent JP501314 desribes a crude enzyme preparation obtained from *Aspergillus oryza* FS1-32 that exhibits major quantities of a non-specific endoproteolytic activity and minor quantities of a proline-specific endoprotease and a carboxypeptidase activity. Incubation of soy bean protein with this crude enzyme preparation is claimed to yield a hydrolysate that is significantly less bitter than a soy bean hydrolysate that can be obtained with another protease preparation which lacks a proline-specific endoprotease in combination with a carboxypeptidase it is suggested in JP5015314 that the activity of the proline-specific endoprotease exposes proline residues that are subsequently removed by the carboxypeptidase. The removal of these hydrophobic, carboxy terminal proline residues by the carboxypeptidase is thought to be essential for obtaining less bitter hydrolysates.

To test this statement, one of the Examples provided in JP5015314 was repeated and the resulting soy hydrolysates were analysed using the above described LC/MS technology rather than evaluating an effect on taste.

According to JP5015314, their incubations with *Aspergillus oryzae* FS, 1-32 contained per gram of substrate the following enzymatic activities.

Protease: in the order of 650 PU; carboxypeptidase: in the order of 0.01 unit and proline-specific endopeptidase: in the order of 0.03 milli-units.

Because the original *Aspergillus oryzae* FS 1-32 preparation was not available, two commercial enzyme preparations, also derived from *Aspergillus oryzae*, were used in the present Example. Moreover, a chromatographically purified proline-specific endoprotease isolated from *Aspergillus niger* (see Example 3) was used to achieve an overdosing of the acid proline-specific endoprotease.

The enzymatic activities of the various preparations were measured according to the procedures provided in JP5015314 and are provided below.

SUMIZYME LP 75.000, a commercial *Aspergillus oryzae* enzyme preparation known to be rich in endoproteolytic activity.
Enzymatic activities as assessed according to the methods of JP5015314:
Protease: 226 PU/gram product; carboxypeptidase: 21 units/gram product; prolyl-endopeptidase: 430 milli-units/gram product FLAVOURZYME 1000 L, a commercial *Aspergillus oryzae* enzyme preparation known to be rich in exoproteolytic activity.
Enzymatic activities as assessed according to the methods of JP5015314:
Protease: 332 PU/gram product; carboxypeptidase: 10 units/gram product; prolyl-endopeptidase: not detectable Chromatographically pure proline-specific endoprotease obtained from *Aspergillus niger* and isolated as described in Example 3.
Enzymatic activities as assessed according to the methods of JP5015314:
Protease: not detectable; carboxypeptidase: not detectable; prolyl-endopeptidase: 45 milli-units/milliliter.

From these data it is evident that although SUMIZYME and FLAVOURZYME are well known for their high proteolytic activities, none of them can provide the same very high ratio of (endo)protease to carboxypeptidase activity as quoted In JP5015314. Surprisingly SUMIZYME, LP 75.000 was found to contain a considerably higher activity of proline-specific endoprotease than the one reported in JP5015314.

The various enzyme preparations were incubated according to the protocol described in JP5015314 but standardised according to the desired carboxypeptidase activity (0.01 unit per gram substrate). Soy isolate (SOYAMIN 90 HV) was used as the substrate in these reactions. After incubation for 5 hours at pH 5 and 50 degrees C., the samples were centrifuged and the supernatants were kept frozen until LC/MS analysis.

LC/MS analysis was carded out as specified in the Materials & Methods section. In this experiment the protein data bank consisted of soy proteins only. The results obtained are specified in Table 1.

TABLE 1

Soy protein treated with several enzymes.

| Enzyme units per gram substrate | Number of peptides analysed | Molar fraction of peptides with proline at C-terminus (%) |
|---|---|---|
| None (reference) | 10 | 0 |
| Sumizyme Protease: 0.11 Carboxypep: 0.01 PEP (milli-units): 0.2 | 39 | 10 |
| Flavourzyme Protease: 0.34 Carboxypep: 0.01 PEP: none | 31 | 6 |
| Sumizyme + *A. niger* Protease: 0.11 Carboxypep: 0.01 PEP (milli-units): 1.5 | 31 | 10 |
| JP5015314 Protease: 650 Carboxypep: 0.01 PEP (milli-units): 0.03 | Unknown | Unknown |

PEP: prolyl-endopeptidase or proline-specific endoprotease.

SUMIZYME LP 75.000 contains a proline-specific endoproteolytic activity which is about 7 times higher than the proline-specific endoproteolytic activity recorded in strain FS 1-32 and yields a molar fraction of approx 10% of soy peptides carrying a carboxy terminal proline. Sumizyme LP 75.000 enriched with the proline-specific endoprotease, isolated from *Aspergillus niger* contains a proline-specific endoproteolystic activity which is about 50 times higher than the activity recorded with strain FS 1-32 but also yields a molar fraction of approx 10% of soy peptides carrying a carboxy terminal proline. These data were confirmed by analysing the number of proline residues which are present in the peptides but not in the carboxy terminal position Flavourzyme contains no detectable proline-specific endpoprotease but yields among the peptides generated and suitable for analysis with the LC/MS technique a molar fraction of 6% of peptides carrying a proline at the carboxy terminal end. If combined with a proline content of approx. 5% of this soy protein Isolate, these three observations indicate that the presence and the activity of the proline-specific endoprotease in combination with the carboxypeptidase activity has a minor effect on the molar incidence of carboxy terminal proline residues only. So, it is hard to imagine that the debittering effect described in JP5015314 and ascribed to a proline-specific endoprotease activity of 0.03 milli-units only, can be linked to a high incidence of peptides carrying proline as the carboxy terminal amino acid residue

EXAMPLE 5

Increased Dosages of Proline-Specific Endoprotease and its Effects on the Hydrolysis of Soy Protein.

In this Example it is demonstrated that high levels of a proline-specific endoprotease are required to generate soy hydrolysates containing a significant amount of peptides carrying a carboxy terminal proline residue. The overall design of these experiments was identical to the ones described in Example 4. Again soy protein isolate was incubated with SUMIZYME LP 75.000 standardised according to the desired carboxypeptidase activity of 0.01 unit per gram soy protein and under conditions described in JP5015314. The incubation took place for either 2.5 or 5.0 hours at pH 5 and 50 degrees C. and was stopped by keeping the material for 10 minutes at 100 degrees C. Subsequently some of the material incubated for 5 hours was obtained and its pH was increased to 7.0. From this material 3 samples were: obtained to which different portions of the *E coli* produced *F. meningosepticum* proline-specific endoprotease were added. To the first sample 1.5 milli-units of proline-specific endoprotease (according to JP5015314 but measured at pH 7.0 and 30 degrees C. to accomodate the pH and temperature optimum of the *E. coli* derived proline-specific endoprotease) were added, to the second sample 150 milli-units were added and to the third sample 15 000 milli-units were added and then the samples were again incubated for 2 hours at 40 degrees C. After incubation the samples were centrifuged and the supernatants were kept frozen until LC/MS analysis. LC/MS analysis took place as specified earlier. The results obtained are specified in Table 2.

TABLE 2

Soy protein treated with high concentrations of proline-specific endoprotease.

| Enzyme in milli-units per gram substrate | Number of peptides analysed | Molar fraction of peptides with Pro at C-terminus (%) |
|---|---|---|
| None (reference) | 4 | 0 |
| Sumizyme 2.5 hours PEP: 0.2 | 26 | 12 |
| Sumizyme 5.0 hours PEP: 0.2 | 27 | 11 |
| Sumizyme 5.0 hours PEP: 0.2 +PEP (*E. coli*) 1.5 | 22 | 14 |
| Sumizyme 5.0 hours PEP: 0.2 +PEP (*E. coli*) 150 | 24 | 17 |
| Sumizyme 5.0 hours PEP: 0.2 +PEP (*E. coli*)15000 | 22 | 36 |

PEP: prolyl-endopeptidase or proline-specific endoprotease.

The results obtained clearly illustrate that a significant increase in the incidence of peptides carrying a carboxy terminal proline residue in the hydrolysate is totally dependent upon the addition of the proline-specific endoprotease. However, only activities which exceed the activity mentioned in JP5015314 and the activity present in SUMIZYME LP 75 000 by several orders of magnitude are capable of doing this. The implication of this observation is that a pure and isolated proline-specific endoprotease is essential to obtain the desired peptide composition of the hydrolysate.

EXAMPLE 6

Molar Incidence of Peptides Carrying Proline as the Carboxy Terminal Residue in Commercial Hydrolysates.

As described earlier, LC/MS/MS can be used for the analysis of the C-terminus of a peptide. With an algorithm in which the peptide's molecular mass (analyzed with LC/MS) and its (partial) amino acid sequence (analyzed with LC/MS/MS) are linked with automatic search procedures within protein databanks, complex peptide mixtures can be analyzed.

In this Example these possibilities were used to analyse a number of commercial infant formulae products as well as commercial protein hydrolysates for the molar incidence of peptides carrying carboxy terminal proline residues which have a molecular weight between 400 and 2000 daltons.

The following products were analysed.
1. NIDAL)® HA 1 (Nestle), containing 11.5 g whey-protein hydrolysates per 100 g powder
2. ALFARE® (Nestle), containing 16.5 g whey-protein per 100 g powder
3. NUTRILON® Pepti Plus (Nutricia), containing 13.5 g whey-protein per 100 g powder
4. NUTRILON® Pepti Junior (Nutricia), containing 16.5 g whey-protein hydrolysates per 100 g powder
5. APTAMIL® HA (Milupa), containing 12.3 g whey-protein and casein hydrolysates per 100 g powder
6. PREGOMIN® (Milupa), containing 13.3 g of probably soy and collagen hydrolysates per 100 g powder
7. NUTRAMIGEN® (Mead Johnson), containing 14.0 g of probably casein hydrolysates 100 g powder
8. VITALARMOR® 800LB (Armor Proteines), containing 100% whey-protein hydrolysates
9. WPH 916 (New Zealand Milk Products), containing 100% whey-protein hydrolysates
10. WE80BG (DMV International), containing 100% whey-protein hydrolysates As the infant formulae contain approx. 15% of protein hydrolysate plus fats (25%) and carbohydrates (50%), a hexane extraction of these products to remove the fat phase proved to be indispensible. The pure hydrolysates could be used as such.

To link the partial protein sequences obtained with sequences of known proteins, a databank containing cow milk protein sequences only was used for all samples except the PREGOMIN sample. The PREGOMIN sample was analysed using a databank containing soy and collagen specific sequence data. For analytical reasons the LC/MS analysis focuses on peptides with a molecular weight ranging from 400 to approx. 2000 Daltons so that peptides outside this range are not taken into consideration.

In each sample between 32 and 76 peptides containing sequence information of the hydrolysed proteins used could be identified. In most samples more than 95% of the 25 most intense peaks in the chromatogram could be related to sequence information of milk proteins. In the PREGOMIN sample only 65% of the 25 most intense peaks could be related to sequence information of soy and collagen proteins. Possible reasons for this are the incorporation of other protein sources in the protein basis or poor MS/MS data due to small or coeluting peaks.

To test the repeatability and the reproducibility of the system, the NUTRILON Pepti Plus sample was extracted twice and analyzed in triplicate (in the beginning of the series, in the middle and at the end). The data obtained from the various analyses on the distribution of the carboxy terminal amino acid residues were found to be in good agreement.

The molar incidence of peptides carrying carboxy terminal proline residues in the various commercial products is provided in Table 3. The molar incidence of such peptides is also related to the proline content of the proteinaceous raw material used for preparing the hydrolysate. For example casein and collagen have much higher proline contents than whey or soy proteins. To take this aspect into account the molar fractions of proline among the amino acids present in the protein basis used for each commercial product has also been deduced using acid hydrolysis followed by amino acid analysis using techniques as described in the Materials & Methods section. Moreover raw material used can differ in their susceptability to enzyme cleavage, for example because of the presence of specific repeating amino acid sequences.

TABLE 3

Molar incidence of peptides carrying carboxy terminal proline in commercial products.

| Infant formulae | Protein basis | Number of peptides analysed | Molar fraction of peptides carrying C-terminal proline (%) | Molar fraction of proline in protein basis (%) |
|---|---|---|---|---|
| Nidal HA 1 | Whey | 49 | 0 | 5 |
| Alfare | Whey | 50 | 2 | 7 |
| N. Pepti Plus | Whey | 74 | 4 | 7 |
| N. Pepti Junior | Whey | 72 | 3 | 7 |
| Aptamil HA | Whey/casein | 69 | 3 | 9 |
| Pregomin | Soy/collagen | 41 | 7 | 8 |
| Nutramigen | Casein | 32 | 22 | 11 |
| Pure hydrolysates | | | | |
| Vitalarmor 800 LB | Whey | 54 | 6 | 6 |
| WPH 916 | Whey | 69 | 0 | 5 |
| WE 80 BG | Whey | 76 | 3 | 8 |

From the data presented in Table 3 it is clear that in the popular whey hydrolysates the molar incidence of peptides carrying carboxy terminal proline residues is low. If we also take the proline content of whey into account, we conclude that none of the commercial whey based products contains a molar fraction of peptides carrying carboxy terminal proline residues which is higher than the molar fraction of proline occurring in the protein basis. Typically the molar fraction of peptides carrying a carboxy terminal proline in these whey based commercial products is 5% or lower.

Looking at the molar incidence of carboxy terminal proline residues in a casein based product like NUTRAMIGEN, we see a substantial higher level than can be found in the whey based products even if the relatively high proline content of casein is taken into account. However, comparing the NUTRAMIGEN product on the one hand with the beta-casein hydrolysate made by incubation with subtilisin and a proline specific endoprotease (see Example 1) shows the vast compositional difference that can occur between an existing commercial casein hydrolysate and a casein hydrolysate according to the invention. Whereas the commercial product (i.e: NUTRAMIGEN) exhibits a molar incidence of peptides carrying a carboxy terminal proline residue of 22%, this figure for the casein hydrolysate according to Example 1 is 61%.

EXAMPLE 7

Molar Incidence of Whey Peptides Carrying Carboxy Terminal Proline in Relation to the Concentration of Proline-Specific Endoprotease Added.

In this Example a commercial whey protein was incubated under various conditions with a proline-specific endoprotease as produced by *E coli*. In the resulting hydrolysate the molar incidence of peptides carrying a carboxy terminal proline residues was determined.

A solution of PROTARMOR 905 (Armor Proteins) in water (10% w/w) was slowly heated up from 25° C. to 60° C. during 1 hour in the presence of 2.5% (weight enzyme/weight substrate) DELVOLASE at pH 8.5. After 1 hour the solution was quickly heated to 80° C. and immediately cooled down to 60° C. after which a new 2.5% dosage of DELVOLASE was added. The hydrolysis was allowed to continue for another hour; then heated to 95° C. for 5 min and cooled again. After adjustment of the pH to 7.4 the proline-specific endoprotease was added in concentrations of 0, 87 and 170 units/gram of substrate (U/g in Table 4; units according to the procedure described in World Journal of Microbiology & Biotechnology, Vol 11, pp 209-212) and hydrolysis was allowed to proceed for another 3 hours at 45° C. At the end the solution was kept at 95° C. for 5 minutes to inactivate the enzyme and to pasteurise the solution. The hydrolysates as obtained were then analysed by LC/MS to determine the molar incidence of carboxy terminal proline residues in the peptides formed as described previously. The results obtained are presented in Table 4.

TABLE 4

Enzyme dosage and molar incidence of peptides carrying carboxyterminal proline.

| Temperature | Dosage of proline-specific endoprotease | Number of peptides analysed | Number of peptides carrying proline in C-terminal position | Molar incidence of peptides with proline at C-terminal position (%) |
|---|---|---|---|---|
| 30° C. | 0 U/g | 40 | 2 | 4 |
|  | 87 U/g | 33 | 12 | 52 |
|  | 170 U/g | 46 | 19 | 53 |
| 45° C. | 0 U/g | 45 | 0 | 0 |
|  | 87 U/g | 49 | 15 | 36 |
|  | 170 U/g | 29 | 13 | 50 |

From this Table, it appears that at 45° C. the molar incidence of peptides carrying proline at their C-terminus increases with the dose of the proline-specific endoprotease. Using the, highest enzyme dosages, up to 50% of the peptides obtained from this whey product could be shown to carry a carboxy terminal proline residue. When the incubation is performed at 30° C., the molar incidence of peptides carrying a carboxy terminal proline residue can reach 52% with 87 units/gram substrate and is hardly increased with higher doses of the enzyme. The higher incidence reached with 87 U/g at 30° C. compared to 45° C. might be explained by a low thermostability of the E. coli enzyme.

EXAMPLE 8

Taste and Composition of Whey Hydrolysates Produced with and without Proline-Specific Endoprotease.

In this Example a proline-specific endoprotease obtained from E. coli was used in combination with subtilisin (DELVOLASE) to produce a whey hydrolysate of low bitterness. Using the data generated in Example 7 the dosage of their proline-specific endoprotease was chosen such that only a marginal increase of peptides carrying carboxy terminal proline residues could be expected. The hydrolysate formed with the proline-specific endoprotease was compared with a similar hydrolysate formed without a proline-specific endoprotease as well as a commercial, low bitter whey hydrolysate. All three products were characterised in terms of taste and their content of peptides carrying a carboxy terminal proline residue.

A solution of PROTARMOR 905 (Armor Proteins) in water (10% w/w) was slowly heated up from 25° C. to 60° C. during 1 hour in the presence of 2.5% (weight enzyme/weight substrate) DELVOLASE at pH 8.5. After 1 hour the solution was quickly heated to 80° C. and immediately cooled down to 60° C. after which a new 2.5% dosage of DELVOLASE was added. The hydrolysis was allowed to continue for another hour; then heated to 95° C. for 5 min and cooled again. After adjustment of the pH to 7.4 the proline-specific endoprotease was added in a concentration of 50 units/gram of substrate. This was allowed to continue for 3 hours at 45° C. According to the data obtained in Example 7 these conditions lead to a marginal increase in peptides carrying a carboxy terminal proline residue only. At the end the solution was kept at 95° C. for 5 minutes to inactivate the enzyme and to pasteurise the solution. Then the solution was cooled down. The same treatment was applied to another sample but without adding the proline-specific endoprotease.

Sensorial analysis of the hydrolysates was carried out in so called two-paired comparison tests. This type of test is used by the American Society of Brewers Chemists (ASBC) to compare the bitterness of 2 different beers. If we accept a 5% risk of error in such a one-sided test, the threshold value for having a statistical difference is 17 out of 24 replies. In each test, the hydrolysates were tasted in 2.5% dry matter concentrations and 1 ml portions of each solution were presented in a disposable vial. Each assessor was asked to rate the bitterness level without swallowing and to rinse the mouth with water afterwards. All samples were coded and allotted at random among the assessors.

The first test was aimed at evaluating the benefit of the combination of subtilisin and the proline-specific endoprotease versus subtilisin alone. The second test was aimed at evaluating the bitterness of the hydrolysate obtained with the combination of subtilisin and proline-specific endoprotease versus a commercial, low bitter hydrolysate (VITALARMOR 800 LB). To that end the VITALARMOR 800 LB was diluted in the same buffer as used for the other hydrolysate to obtain a comparable protein concentration.

Of the 24 persons participating in the first test, 17 rated the sample obtained with the combination of subtilisin and proline-specific endoprotease as less bitter than the sample obtained with subtilisin alone. This result is statistically significant and confirms the debittering activity of a proline-specific endoprotease, even if applied at relatively low concentrations (cf Example 7). Worthwile to note is that these "low" enzyme concentrations are several-orders of magnitude higher than the enzyme dosages applied in patent JP5015314 and for which a debittering effect was claimed.

In the second paired sample comparison, 19 out of the 24 participants rated the sample treated with the combination of subtilisin and proline-specific endoprotease as less bitter than the commercial VITALARMOR 800 LB product. The latter observation is statistically also significant and illustrates the economical value of the hydrolysates and enzyme mixtures of the invention.

The hydrolysates obtained with or without the proline-specific endoprotease were analysed by LC/MS as described before. In the hydrolysate obtained with the subtilisin alone, 41 peptides were analysed. It came out that none of these peptides carried a carboxy terminal proline residue despite the fact that 18 peptides were shown to contain at least one proline residue.

In the hydrolysate obtained with the combination of subtilisin and proline-specific endoprotease 31 peptides were analysed and 6 were shown to carry a carboxy terminal proline residue. This observation, which is in line with what could be expected on the basis of the results obtained in Example 6, shows that as the result of the incubation with the proline-specific endoprotease the molar incidence of peptides bearing a carboxy terminal proline residue was increased from 0 to 19%. As the sensory analysis of the latter products has demonstrated a statistically significant reduced bitterness, this experiment clearly links a slight increase in the molar incidence of carboxy terminal proline residues with reduced bitterness.

Apart from decreasing the level of bitterness, this incubation with a low level of proline-specific endoprotease could also be shown to decrease the peptide length of the hydrolysate. In the hydrolysate treated with DELVOLASE alone, the LC/MS analysis revealed that peptides vary in length from 4 to 14 amino acids with an average length of 7.5 amino acids. In the hydrolysate treated with the combination of DELVOLASE and the proline-specific endoprotease, the peptide length could be shown to vary from 4 to 12 amino acids with an average length of 6:1 amino acids. These reduced peptide lengths will not only improve the yield of the hydrolysate production process, but also reduce the overall allergenicity of the hydrolysate and minimise precipitation under acid conditions.

EXAMPLE 9

Cloning of the Proline-Specific Endoprotease from *Aspergillus niger*

Forward and reverse oligonucleotide primers were developed using the peptide sequences that were elucidated in Example 3. To reduce degeneracy of the primers, inosine bases were introduced at several positions. This increases the abundance of oligonucleotide primers in the pool that are able to prime a PCR reaction, but the disadvantage is that the specificity of the reaction decreases.

Genomic DNA from *A. niger* G306 (deposited as CBS109712 with the CBS on Sep. 10, 2001) was isolated using standard techniques and used as template in PCR reaction with the oligonucleouide primers indicated in Table: 5'

TABLE 5

Peptide- and oligonucleotide primers of endo-Pro (I = inosine)

| Peptide | Primer | No. |
|---|---|---|
| ATTGEAYFE (SEQ ID NO: 3) | 5'-GCIACIACIGGIGARGCITAYTTYGA-3' (SEQ ID NO: 4) | 1 |
|  | 5'-TCRAARTAIGCYTCICCIGTIGTIGC-3' (SEQ ID NO: 5) | 2 |
| ATVNSWTGGWDFTR (SEQ ID NO: 6) | 5'-TGGACIGGIGGITGGGAYTTYAC-3' (SEQ ID NO: 7) | 3 |
|  | 5'-GTRAARTCCCAICCICCIGTCCA-3' (SEQ ID NO: 8) | 4 |
| DGAPEGTST (SEQ ID NO: 9) | 5'-GAYGGIGCICCIGARGGIAC-3' (SEQ ID NO: 10) | 5 |
| 5'-GTICCYTCIG-GIGCICCRTC-3' |  | 6 |
|  | (SEQ ID NO: 11) |  |
| EREAGAAVTP (SEQ ID NO: 12) | 5'-GARGCIGGIGCIGCIGTIACICC-3' (SEQ ID NO: 13) | 7 |
|  | 5'-GGIGTIACIGCIGCICCIGCYTC-3' (SEQ ID NO: 14) | 8 |

In the experiment all possible combinations of forward and reverse primers were used to amplify the gene encoding the proline specific endoprotease from *A. niger*. Initial experiments were performed under standard PCR conditions (denaturation at 94° C., annealing at 55° C. and extension at 72° C.). Surprisingly these experiments did not yield any specific PCR product. Since a negative result might also be due to impurities in the template DNA, we performed control PCR reactions using PCR primers for several different but known *A. niger* genes: In comparable reactions these latter genes could be successfully amplified from *A. niger* G306 genomic DNA showing that the inability, to amplify a fragment using the endo-Pro primers was not due to impurities in the genomic DNA preparation.

Subsequently it was decided to decrease the stringency of the PCR reaction by decreasing the annealing temperature down to 45° C. Consequently the specificity of the PCR was decreased and several bands were amplified, although most of these bands were also detected in control PCR reactions lacking one of the primers. Several of these PCR products were cloned into the general cloning vector pCR2.1 (Invitrogen, Groningen, The Netherlands), and the DNA sequence of these fragments was determined. Unfortunately none of the cloned fragments coded for the gene encoding proline specific endoprotease.

Additionally, many other adjustments to the PCR protocol were made such as the use of a different polymerase, increasing primer- or template-concentration, a touch-down PCR and introduction of a hot start, but none of these protocols yielded a specific fragment of the gene encoding the proline specific endoprotease. To minimize the obvious risks of this uncertain approach, it was decided to try another less well known cloning procedure.

3'-RACE

Since none of our attempts to amplify the gene encoding the proline specific endoprotease from *A. niger* G306 genomic DNA were successful, we decided to use a different approach in which RNA is used as the template for cDNA synthesis. The approach of cloning an unknown gene using 3'-RACE, 5'-RACE and amplification of the complete open reading frame, has been described in WO9938956. The advantage of this procedure, compared to the direct PCR procedure described above, is that an additional priming site is introduced at the 3'-end of the cDNA, so that only a single gene-specific oligonucleotide plus an universal primer is required to amplify part of the coding sequence, instead of two degenerate primers. Additionally, using cDNA as template circumvents problems in amplification due to introns. The use of cDNA as template in the amplification reaction also increases the concentration of the template compared to amplification from genomic DNA.

According to this approach, *A. niger* G306 was grown in a medium containing collagen as sole carbon source to induce the expression of the gene encoding for proline specific endoprotease. Medium composition is described in the Materials and Methods section. Young mycelium was harvested after 48 hr growth at 34° C., and used for the isolation of total RNA. To this end, mycelium was harvested using filtration through Miracloth filtration wrap and washed with ice cold sterile demiwater. Mycelium (250 mg) was frozen immediately in liquid nitrogen and ground to a fine white powder using mortar and pestle. The white powder was transferred to a sterile 15 ml Greiner tube and total RNA was isolated with the Trizol method exactly as described by the supplier (Life Technologies, Paisley, UK).

The RNA preparation was used to synthesize cDNA from the anchor primer of the 3'-RACE kit (AP; Life Technologies), extending cDNA from the poly-A tail of mRNA. After RNase H treatment, cDNA was amplified by PCR with the abridged universal amplification primer (AUAP; Life Technologies) and the inosine substituted gene specific forward primers (No. 1, 3, 5, and 7) described above. Only with primer No. 1 plus AUAP a specific amplification product of ~1.4 kb could be amplified from *A. niger* G306 RNA. With the other primers only non-specific amplification at low stringency was obtained. This 1.4 kb cDNA fragment was cloned into pCR2.1 and the DNA sequence was determined.

5'-RACE

From this sequence three gene specific primers were designed for further amplification of the 5'-part of the gene. All three primers, 5'-TTCAGTACTCCACCAGTACCTC-3' (SEQ ID NO: 18),5'-TGGGAAAAGGTGCCCTTCTCC-3' (SEQ ID NO: 19),and 5'-GGATTATGATGGTCCAGCAGC-3' (SEQ ID NO: 20), were complementary and reverse to the coding sequence of the gene coding for proline specific endoprotease.

Total RNA from *A. niger* G306 was used to synthesize cDNA with the 5'-RACE kit (Life Technologies) using primer 5'-TTCAGTACTCCACCAGTACCTC-3'(SEQ ID NO: 18). After RNase treatment, cDNA was purified using the Glasmax cartridge (Life Technologies). A polydC tail was added to the cDNA using terminal transferase (TdT; Life Technologies). The cDNA was amplified in a PCR reaction using the abridged anchor primer (AAP; Life Technologies) and with the first nested primer 5'-TGGGAAAAGGTGCCCT-TCTCC-3' (SEQ ID NO: 19). A second amplification reaction using the AUAP primer (Life Technologies) and a second primer 5'-GGATTATGATGGTCCAGCAGC-3' (SEQ ID NO: 20) was required to obtain a specific amplification product of ~0.25 kb. This fragment was purified via agarose gel electrophoresis and cloned into pCR2.1 and the DNA sequence was determined. This showed that this fragment contains the 5'-part of the gene coding for the proline specific endoprotease.

Characterization of the Gene

Combining the overlapping sequences of the 3'-RACE and the 5'-RACE results in the complete coding sequence, of the gene encoding the proline specific endoprotease. SEQ ID 1 shows the entire sequence of the open reading frame of this gene. The deduced protein sequence of 526 amino acids is depicted in SEQ ID-2. Peptide ATTGEAYFE (SEQ ID NO: 3) appeared to be completely correct. Peptide DGAPEGTST (SEQ ID NO: 9) is also correct but is encoded by genomic DNA that is interrupted by an intron (see SEQ ID 15 and example 11 for the cloning and sequence of genomic DNA of *Aspergillus niger* CBS513.88). The other two peptides incorporate errors due to the LC/MS/MS approach which has been used for their characterization (see Example 3). Despite these uncertainties we successfully selected and identified the desired genetic information encoding the proline specific endoprotease from *Aspergillus* for the first time.

The novelty of the proline specific endoprotease from *Aspergillus* was confirmed by BLAST searches to well known databases such as SwissProt, PIR and trEMBL. No strong identity of this protein with any other protein can be detected when compared to the protein sequence databases.

EXAMPLE 10

Overexpression of the Gene Encoding Proline Specific Endoprotease and Isolation of the Proline Specific Endoprotease The entire open reading frame of the gene encoding proline specific endoprotease was PCR amplified from cDNA of *A. niger* G306 using the primers 5'-ATGCGTGCCTTCTC-CGCTGTC-3' (SEQ ID NO: 21) and the AUAP primer (Life Technologies). The obtained PCR fragment was cloned into the cloning vector, pCR2.1 (Invitrogen). The resulting plasmid was digested with EcoRI and the fragment containing the endo-Pro gene was cloned into the EcoRI site of expression vector pGBFIN-11 (WO9932617). The resulting clones were checked by restriction with XhoI, which yields a fragment of ~0.65 kb when the fragment is inserted in the correct orientation. The resulting plasmid is shown in FIG. 1 and was named pGBFIN11-EPO.

*A. niger* CBS 513.88 was used as host for the over-expression of the gene encoding the proline-specific endoprotease. Therefore, the expression vector pGBFIN11-EPO was linearized by digestion with NotI, which removes all *E coli* derived sequences from the expression vector. The digested DNA was purified using phenol:chloroform:isoamylalcohol (24:23:1) extraction and precipitation with ethanol. The *A. niger* transformation procedure is extensively described in WO 98/46772. It is also described how to select for transformants on agar plates containing acetamide, and to select targeted multicopy integrants. Preferably, *A. niger* transformants containing multiple copies of the expression cassette are selected for further generation of sample material.

Cultivation and Isolation of Protease

An *A. niger* strain containing multiple copies of the expression cassette was used for chromatographic generation of sample material by cultivation of the strain in shake flask cultures. A useful method for cultivation of *A. niger* strains and separation of the mycellum from the culture broth is described in WO 98/46772. The culture broth obtained was analyzed on SDS-PAGE which is depicted in FIG. 2 Subsequently, the culture broth was used for chromotograhpic purification of the protease to remove any contaminating endo- and exoproteolytic activities. To that end the fermentation broth was first centrifuged to remove the bulk of the fungal mass and the supernatant was then passed through a number of filters with decreasing pore sizes to remove all cell fragments. Finally, the ultrafiltrate obtained was diluted ten times in 20 millimol/liter sodium acetate pH 5.1 and applied on a Q-Sepharose FF column. Proteins were eluted in a gradient from 0 to 0.4 moles/liter NaCl in 20 millimol/liter sodium acetate pH 5.1. Peak fractions displaying activity towards the cleavage of Z-Gly-Pro-pNA (Bachem, Switzerland) were collected and pooled, according to the protocol described in World Journal of Microbiology & Biotechnology 11, 209-212 (1995), but under slightly modified assay conditions. Taking the acid pH optimum of the *A. niger* derived proline-specific endoprotease into account, the enzyme assay was carried out at pH 5 in a citrate/phosphate buffer at 37° C. Pooling of the active fractions followed by concentration finally yielded a preparation which showed only a single band on SDS-PAGE and one peak on HP-SEC. Further analysis by hydrophobic interaction chromatography confirmed the purity of the enzyme preparation obtained.

Furthermore, the purified proline specific endoprotease was used for the determination of the amino-terminus of the mature protein, by Edman degradation. The amino-terminus of the mature proline-specific endoprotease starts at position 42 in SEQ_ID 2 and SEQ_ID__17.

EXAMPLE 11

Screening of Fungal Species Other than *A. niger* for the Presence of the Gene Encoding the Proline-Specific Endoprotease.

On the basis of the low nucleotide sequence homology between the *F. meningosepticum* and the *A. niger* gene encoding proline specific endoprotease, cross hybridization between these two genes can be excluded. To get an impression of the conservation of the *A. niger* specific nucleotide sequence in more related microorganisms, the following strains were selected for a hybridization experiment. The fungal species *Aspergillus niger* CBS102.12, *Aspergillus niger* CBS513.88, *Aspergillus niger* G306, *Aspergillus carbonarius* ATCC1025, *Aspergillus sojae* DSM2809, *Aspergillus ochraceus* ATCC18500, *Aspergilus acculeatis* CBS101.43, *Verticillium psalliotae* CBS396.58, *Phialophora mustea* CBS142.41, *Penicillium chrysogenum* URCM237, *Phoma exigua* CBS431.74, *Microsporum gallinae* CBS221.55, *Acremonium strictum* ATCC20371, *Rhizomucor miehei* CBS370.65, *Alternaria alternata* CBS103.33, *Talaromyces emersonli* CBS393.64, *Cladosporium chlorocephalum* CBS213.73, *Cladosponum tenuissinum* CBS 117.79, and *Trichoderma reesii* ATCC26921 were cultivated in 100 ml PDB (Potato Dextrose Broth, Difco) at 30° C. (except for the *Talaromyces* strain which was grown at 50° C.) and shaken at 220 rpm.

When cultures were sufficiently grown, mycelial mass was harvested by filtratlon through Miracloth filter, washed with 10 mM KPi buffer (pH 7.0) and dried between filterpaper. Mycelium was ground under liquid nitrogen with a mortar and pestle, until a fine white powder was obtained. Subsequently, chromosomal DNA was isolated using the PureGene kit (Gentra Systems, Minneapolis USA) according to instructions by the supplier.

*Saccharomyces cerevisiae* ATCC20785 was used as negative control in the experiment and cultivated in YePD at 30° C. and shaken at 220 rpm.

For preparation of a Southern blot, chromosomal DNA of all species was digested with XhoI and restriction fragments were separated by agarose gelelectrophoresis on a 0.8% agarose gel in TAE buffer. After separation, DNA fragments were blotted to nitrocellulose (0.2 µm, Schleicher & Schuell) membranes by conventional procedure (Sambrook et al. (1982): Molecular cloning; a laboratory manual, ISBN 0-87969-309-6), and the blot was backed for 2 hours at 80° C.

The probe for hybridization was synthesized with PCR on pGBFIN11-EPO as template using primers 5'-ATGCGTGC-CTFCTCCGCTGTC-3' (SEQ ID NO: 21) and the AUAP primer. About 30 nanograms of the cDNA fragment was labeled with $^{32}$P-alpha-dATP (Amersham, England) with the RadPrime DNA labeling system (Life Technologies) according to the suppliers instructions. After labeling unincorporated dNTPs were removed by purifying the probe fragment over a Sephadex G-50 column according to the spun column procedure (Sambrook et al., 1982).

Prior to adding to the hybridisation mixture, the purified probe was denatured by incubation in boiling water for 5 minutes followed by rapid cooling in ice, and used immediately.

Prehybridization of the blots was in 50 ml 6×SSC, 0.5% SDS, 5× Denhardt, 0.1 mg/ml Herring sperm DNA (Life Technologies) for 1 hour at 50° C. under continuous agitation. After addition of the probe to the prehybridization solution, hybridization was performed for 16 hours at 50° C. The blots were washed twice with 200 ml 6×SSC, 0.1% SDS for 30 minutes at ambient temperature, and once with 200 ml 6×SSC, 0.1% SDS for 30 minutes at 50° C., to remove a specific hybridization to the blot X-Omat AR (Kodak) films were used to visualize the hybridization.

The results of this experiment are depicted in Table 6. *A. niger* and *A. carbonarius* strains give strong hybridization with the probe. Also other *Aspergillus* strains like *A. sojae*, *A. ochraceus* and *A. acculeatis* give hybridization with the probe. Apparently the gene encoding the proline-specific endoprotease is well conserved within the *Aspergillus* genus.

Surprisingly, also fungi that are more distant from *Aspergillus*, like *Phialophora mustea*, *Rhizomucor miehei*, *Alternaria alternata*, *Talaromyces emersonii*, and *Trichoderma reesii* give good hybridization to the cDNA of the proline-specific endoprotease. *Saccharomyces cerevisiae* which was included as negative control, as well as a few other species do not show any hybridization with the cDNA from *A. niger* (see Table 6). This result shows that the gene encoding the proline-specific endoprotease is conserved in many fungal species, and a person skilled in the art will understand that the genes from these species can be isolated using the heterologous hybridization shown here as detection method.

To illustrate this, the cDNA fragment of *Aspergillus niger* G306, used in this example, was used as probe for the screening of a genomic DNA library of *Aspergillus niger* CBS513.88. A person skilled in the art will have knowledge to generate a genomic DNA library, and to screen such a library with a labelled DNA probe. This procedure has also been described extensively in literature (Sambrook et al. (1989) Molecular Cloning; a laboratory manual. Cold Spring Harbor Laboratory Press). Positive clones in the screening were purified and the DNA was sequenced. *Aspergillus niger* CBS513.88 genomic DNA coding for the proline-specific endoprotease is represented in SEQ_ID 15. This example illustrates that it is possible to isolate the gene coding for the proline-specific endoprotease from other species and strains using hybridization to the cDNA of this gene from *Aspergillus niger* G306.

The deduced coding sequence and amino-acid sequence of the proline-specific endoprotease of CBS513.88 is depicted in SEQ_ID 16 and SEQ ID_ID 17 respectively.

TABLE 6

Heterologous hybridization of the *A. niger* endo-Pro gene to chromosomal DNA of various fungi.

| Species | Hybridization |
| --- | --- |
| *Aspergillus niger* CBS102.12 | +++ |
| *Aspergillus niger* CBS513.88 | +++ |
| *Aspergillus niger* G306 | +++ |
| *Aspergillus carbonarius* ATCC1025 | +++ |
| *Aspergillus sojae* DSM2809 | + |
| *Aspergillus ochraceus* ATCC18500 | ++ |
| *Aspergilus acculeatis* CBS101.43 | + |
| *Saccharomyces cerevisiae* ATCC20785 | − |
| *Verticillium psalliotae* CBS396.58 | − |
| *Phialophora mustea* CBS142.41 | + |
| *Penicillium chrysogenum* URCM237 | − |
| *Phoma exigua* CBS431.74 | − |
| *Microsporum gallinae* CBS221.55 | − |
| *Acremonium strictum* ATCC20371 | − |
| *Rhizomucor miehei* CBS370.65 | + |
| *Alternaria alternata* CBS103.33 | + |
| *Talaromyces emersonii* CBS393.64 | + |
| *Cladosporium chlorocephalum* CBS213.73 | − |
| *Cladosporium tenuissinum* CBS117.79 | − |
| *Trichoderma reesii* ATCC26921 | + |

EXAMPLE 12

Enzyme Mixture Obtained from *Aspergillus oryzae* FS 1-32 and its Effects in the Hydrolysis of Soy Protein.

Japanese patent JP5015314 discloses a crude enzyme preparation obtained from *Aspergillus oryzae* FS 1-32 containing major quantities of a non-specified endoproteolytic activity and minor quantities of a proline-specific endoprotease. This crude preparation further contains a significant carboxypeptidase activity. Upon incubation of soy bean protein with this crude enzyme preparation, a soy bean protein hydrolysate is obtained that is claimed to be significantly less bitter than a soy bean hydrolysate that can be obtained with other protease preparations. The explanation given in JP5015314 for this beneficial debittering effect is that other protease preparations lack the presence of a proline-specific endoprotease in combination with a carboxypeptidase. JP5015314 suggests that the basis for the debittering effect is the removal of the proline residues that are exposed by the activity of the proline-specific endoprotease and subsequently removed by the carboxypeptidase.

Example 4 of the present application describes the effects on soy protein of a mixture of commercial enzymes resembling the proteolytic activity profile of strain A. oryzae FS 1-32. One of the conclusions of this experimental work is that the incorporation of a proline-specific endoproteolytic activity in levels as recorded with strain FS 1-32 does not lead to an appreciable increase in soy peptides carrying a carboxyterminal proline residue. As this conclusion has important implications regarding the non-bitter protein hydrolysates described in the present application, we decided to repeat the experiment but using the enzyme mixture as obtained from A. oryzae FS 1-32 and under conditons as described in JP5015314.

Aspergillus oryzae FS 1-32 (as obtained from depot 12193 of the Micr. Ind Lab in Japan) was plated on malt extract agar plates, incubated for four days at 35° C. and then stored for one day at 4° C. Spores from these plates were used to inoculate the inoculation medium containing 20 grams/kg of dextrose, 15 grams/kg of defatted soy flour, 5 grams/kg of low salt yeast extract, 1 gram/kg of KH2PO4 and 0.2 grams/kg of antifoam. After dissolution in demineralised water, the pH of the medium was adjusted with sulphuric acid to 5.5 and then divided in portions of 20 ml over 100 ml shakeflasks with baffles. Shakeflasks with medium were sterilized for 30 minutes at 121° C. and inoculated after cooling down. After two days in a shake incubator at 32° C., 1 ml was used to inoculate another 100 ml inoculation medium. After another day in the shake incubator at 32° C. this culture was used to inoculate the culture medium. Because JP501314 does not provide information regarding the fermentation procedures used, the fermentation protocol and medium as provided in EP 0 522 428 has been used.

The culture medium according to EP 0 522 428 contains the following components: acid casein (Armor Proteins, France) 25.4 grams/liter, roasted soybean flour (Cargill, Netherlands) 8.6 grams/liter, wheat bran (Zonnatura, Netherlands) 15.0 grams/liter, corn starch 20.0 grams/liter, tannic acid (Omnichem) 16.0 grams/liter and $KH_2PO_4$ 26.6 grams/liter. Because the recommended tannic acid (to stimulate the formation of the proline-specific endoprotease) was not specified in EP 0522428, two kinds of tannic acids, i.e. BREWTAN C and TANAL W2 (both from Omnichem (Wetteren, Belgium) were used. Finally the pH value of the culture medium was adjusted with phosphoric acid (20%) to 4.5 and then divided in portions of 100 ml in 500 ml shake flasks with baffles. Flasks were sterilized for 30 minutes at 121° C.

After inoculation with 1 milliliter of the pre-grown inoculation medium, the cultures were incubated for 2 and 4 days at 32° C., 250 rpm. To remove the biomass, the culture broths were filtered over a Whatman glass microfibre filter (cat no 1820090) which were then stored at −20° C. Part of this frozen material was lyophilized and used for activity measurements as well as incubations with soy protein.

The activities of the prolyl-endopeptidase, carboxypeptidase and endoprotease in the lyophilized materials were measured exactly as described in JP5015314. The samples that had been fermented for 2 days showed appreciably higher enzyme activity levels then the samples that had been fermented for the recommended 4 days so that it was decided to use these 2 days samples for the final incubation with soy protein. Enzyme activity data of those samples showing the highest prolyl-endopeptidase activities are shown hereunder.

TABLE 7

| | Enzyme activities per gram of lyophilized material | | |
|---|---|---|---|
| Sample | Prolyl-endopeptidase activity [mU/g] | Carboxypeptidase activity [U/g] | Protease activity [PU/g] |
| 1 +Brewtan | 2.87 | 4.99 | 609 |
| 3 +Tanal | 2.38 | 3.68 | 595 |
| 4 +Tanal | 6.30 | 7.79 | 592 |

The propyl-endopeptidase and the carboxypeptidase, activities measured in the samples 1, 3 and 4 are comparable with figures provided in JP5015314. However, the endoprotease activities measured in these samples turned out to be about 200 times lower than indicated in JP501314. In view of the endoproteolytic activities reported in various industrial enzyme preparations (see Example 4); the extremely high endoproteolytic activities obtained with A. oryzae FS 1-32 and specified in JP5015314 are probably unrealistic.

In an attempt to copy Example 2 of JP5015314 as precisely as possible, the following experiment was carried out. Ten grams of soy protein SOYAMIN 90HV (Lucas Meyer, Hamburg, Germany) were suspended in 100 ml demineralised water and the pH was adjusted with 4N NaOH to 8.5. Then 0.5 g DELVOLASE (DSM Food Specialities, Seclin, France) was added (instead of Protin AY from Daiwa Kasei; both DELVOLASE and Protin AY are Bacillus-derived alkaline endoproteases) and the protein solution was incubated for 2 hours at 60° C. (in JP5015314 the incubation time and temperature with Protin AY are not specified). Finally the DELVOLASE was inactivated by heating the solution for 10 minutes at 92° C.

The resulting protein hydrolysate was then incubated with the enzyme samples 1, 3 and 4 according to the protocol described in JP5015314 but standardised according to the desired carboxypeptidase activity (0.01 unit per gram substrate). The implication was that per gram of soy isolate 2.0 milligrams of lyophilized enzyme sample 1 had to be added, 2.7 milligrams of lyophilized enzyme sample 3 and 1.3 milligram of lyophilized enzyme sample 4. The resulting endoprotease and prolyl endoprotease activities are presented in Table 8.

After incubation for 5 hours at pH 5 and 50 degrees C., the samples were centrifuged and the supernatants were kept frozen until LC/MS analysis.

LC/MS analysis was carried out as specified in the Materials & Methods section.

In this experiment the protein data bank consisted of soy proteins only. The frequency of carboxyterminal proline residues detected in the peptides obtained are specified underneath.

TABLE 8

Soy protein treated with several enzymes.

| Enzyme units per gram substrate | Number of peptides analysed | Molar fraction of peptides with proline at C-terminus (%) |
|---|---|---|
| None (reference) | 73 | 3 |
| Sample 1 (2.0 mg) Protease (PU): 1.20 Carboxypep (U): 0.01 PEP (milli-Units): 0.006 | 76 | 1 |
| Sample 3 (2.7 mg) Protease (PU): 1.60 Carboxypep (U): 0.01 PEP (milli-Units): 0.006 | 78 | 3 |
| Sample 4 (1.3 mg) Protease (PU): 0.80 Carboxypep (U): 0.01 PEP (milli-units): 0.008 | 70 | 2 |
| JP5015314 Protease: 650 Carboxypep: 0.01 PEP (milli-units): 0.03 | | |

PEP: prolyl-endopeptidase or proline-specific endoprotease.

From the data obtained it is obvious that the incubation of soy protein with the crude enzyme preparation obtained from *Aspergillus oryzae* FS 1-32 does not result in a significant increase of the molar fraction of peptides carrying a carboxy-terminal proline residue. So the debittering effect described in JP5015314 cannot be attributed to a high incidence of such peptides in the final hydrolysate.

EXAMPLE 13

A Non-Bitter Casein Hydrolysate Obtained by Combining Thermolysin with a Proline-Specific Endoprotease from *Aspergillus*.

Proline specific endoprotease from *A. niger* G306 was overexpressed and chromatographically purified (see Example 10) and subsequently used to produce a non-bitter casein hydrolysate. To that end we added to 100 mL of a solution of sodium caseinate (MIPRODAN 30) containing 60 grams per liter, 100 mg of thermolysin (THERMOASE). Incubation at pH 6.7 and 85 degrees C. resulted in an immediate flocculation and precipitation of caseinaceous protein. Incubation for two hours finally; resulted in a clarified solution still containing some precipitate. Then the pH of the solution was adjusted to pH 5.0 and the THERMOASE was inactivated by heating for 45 min at 95 degrees C. After cooling down, the solution was tasted and observed to be very bitter. In this stage the DH (Degree of Hydrolysis; established using the TNBS method) of the caseinate solution was approx 35%. Analysis of 64 peptides by LC/MS/MS using a databank for bovine caseinates indicated a molar incidence of pepides carrying a carboxyterminal proline residue of 14%.

Then 3 units of the chromatographically purified proline specific endoprotease from *A. niger* were added to 25 millilitres of the hydrolysate. After incubation for 20 hours at 50 degrees C., another enzyme inactivation cycle was carried out by heating the solution for 30 minutes at 90° C. After cooling to room temperature the solution was decanted and the clear supernatant was adjusted to a pH value to 4.0; the caseinate hydrolysate was found to remain completely dissolved and clear. Tasting demonstrated the absence of any bitterness or off-flavors. The DH of this final hydrolysate using the TNBS method was approx 50%; LC/MS/MS analysis of 64 peptides showed that the molar incidence of peptides carrying a carboxyterminal proline residue was increased to 45%. This 45% is almost 4 times higher than the molar fraction of proline occurring in the MIPRODAN substrate.

The invention claimed is:

1. A protein hydrolysate which comprises peptides, wherein the molar fraction of peptides carrying a carboxy terminal proline is more than two times the molar fraction of proline in a protein substrate used to generate the protein hydrolysate, and wherein the protein substrate is selected from the group consisting of whey, casein and soy.

2. A protein hydrolysate according to claim 1, wherein the molar fraction of peptides carrying a carboxy terminal proline is at least three times the molar fraction of proline in the protein substrate.

3. A protein hydrolysate according to claim 1, wherein the average peptide length is from 3 to 9 amino acids.

4. A protein hydrolysate according to claim 1, wherein at least 10% of the protein substrate is hydrolysed.

5. A protein hydrolysate comprising peptides selected from the group consisting of
 a whey hydrolysate wherein the molar fraction of peptides carrying a carboxy terminal proline is at least 8%;
 a casein hydrolysate wherein the molar fraction of peptide carrying a carboxy terminal proline is at least 25%; and
 a soy hydrolysate wherein the molar fraction of peptide carrying a carboxy terminal proline is at least 20%.

6. A food or drink which comprises a protein hydrolysate according to claim 1.

7. The food or drink of claim 6 which comprises from 5% to 10% (w/v) of the protein hydrolysate.

8. The food or drink of claim 6 that has reduced bitterness and/or low antigenicity.

9. The food or drink of claim 8 which comprises an infant formula.

10. A method of enzymatically producing a protein hydrolysate from a protein substrate, which method comprises incubating the protein substrate with sufficient proline-specific endoprotease to produce a protein hydrolysate which comprises peptides, wherein the molar fraction of peptides carrying a carboxy terminal proline is more than two times the molar fraction of proline in the protein substrate used to generate the protein hydrolysate, and wherein the protein substrate is selected from the group consisting of whey, casein and soy.

11. A method according to claim 10, wherein said incubating is performed either sequentially or concomitantly with the proline-specific endoprotease and one or more other endoprotease(s).

12. A method according to claim 11, wherein the other endoprotease(s) is a serine or a metallo-endoprotease or a combination of a serine and a metallo-endoprotease.

13. A method according to claim 10, wherein the method further comprises recovering the protein hydrolysate without ultrafiltration or a microfiltration.

14. A method according to claim 12, wherein the other endoprotease(s) is a combination of subtilisin and carboxypeptidase.

15. A method according to claim 7, wherein the molar fraction of peptides carrying a carboxy terminal proline in the protein hydrolysate is more than three times the molar fraction of proline in the protein substrate.

16. A method according to claim 10, wherein the method employs at least 150 milli-units of proline-specific endoprotease per gram substrate.

17. A method according to claim 10, wherein the proline-specific endoprotease has a pH optimum below 7.

18. A method according to claim 10, wherein the proline-specific endoprotease is from *A. niger*.

19. A food or drink which comprises a protein hydrolysate according to claim 5.

20. A food or drink of claim 19 which comprises from 5% to 10% (w/v) of the protein hydrolysate.

21. A food or drink of claim 19 which has reduced bitterness and/or low antigenicity.

22. A method according to claim 10, wherein the average peptide length is from 3 to 9 amino acids.

23. A method according to claim 10, wherein at least 10% of the protein substrate is hydrolysed.

* * * * *

SEQUENCE LISTING

<160> NUMBER OF SEQ ID NOS: 21

<210> SEQ ID NO 1
<211> LENGTH: 1581
<212> TYPE: DNA
<213> ORGANISM: Aspergillus niger G306

<400> SEQUENCE: 1

```
atgcgtgcct tctccgctgt cgctgctgcg gccctggcgc tctcttgggc gtctctggct      60
caggctgctc gccccgtct tgtgcccaag cctgtctctc ggccagcctc gagtaaatcg     120
gctgcgacca cgggcgaggc ttactttgag cagctgctgg accatcataa tccggagaag     180 ggcaccttt cccagaggta ctggtggagt actgaatact ggggtggtcc tgggtcaccg      240
gtcgtcctct ttactcctgg agaggtctct gccgatggct atgaggggta tctcaccaat     300
gggactctca ctggtgtcta tgcgcaggag atccagggtg ccgtcattct cattgagcac     360
cgctactggg gtgattcttc tccttatgag gtgctcaatg ccgaaactct tcagtacctc     420
acactggacc aagccattct ggacatgacc tacttcgccg agacggtgaa gctgcaattc     480
gataacagca cccgcagcaa tgcgcagaat gctccctggg tcatggtcgg tggatcatac     540
agtggtgcct tgacggcttg gaccgaatct gtcgcgcctg gaacgttctg ggcttaccat     600
gccactagtg ctcctgtgga ggctatctac gactattggc aatacttta ccccatccag      660
```

-continued

```
caaggtatgg cacagaactg cagcaaggac gtgtctctgg tagccgagta tgtcgacaag    720
attggaaaga acggaactgc caaggagcag caggcactca aggaattgtt tggtctggga    780
gctgttgagc attttgatga ctttgccgct gtcctcccca acggaccgta cctctggcaa    840
gacaacgact ttgccacggg atactcttcc ttcttccagt tctgtgacgc cgtcgagggt    900
gtcgaagccg cgcggcagt aaccccggc cccgagggtg tcggcctcga aaaggccctg      960
gccaactacg caaactggtt caattcaacc attctccctg attactgcgc aagctacggc   1020
tactggaccg acgaatggag cgtcgcctgc ttcgacagct acaacgcctc gagcccatc    1080
tacaccgata cctccgtagg caatgccgtc gaccgccaat gggaatggtt cctctgcaac   1140
gagcctttct tctactggca ggacggtgct cccgagggta cctccaccat tgtgccccga   1200
ctcgtcagcg cctcctactg caacggcaa tgtccgctct acttccccga aacgaacggc    1260
tacacgtacg cagcgcgaa gggtaagaac gccgccacgg tgaacagctg accggtgga    1320
tgggatatga cccgcaacac gacgcggttg atctggacga acgggcaata tgaccccgg    1380
cgggactccg gtgtgtcgag cactttccgg cccggtggac cgctggcgag cacggcgaat   1440
gaacccgtgc agattatccc gggcggattc cattgctcgg atttgtatat ggcggattat   1500
tatgcgaatg aggggttaa aaaggtggtg gataatgagg tgaagcagat caaggagtgg    1560
gtggaggagt attatgcctg a                                             1581
```

<210> SEQ ID NO 2
<211> LENGTH: 526
<212> TYPE: PRT
<213> ORGANISM: Aspergillus niger G306

<400> SEQUENCE: 2

```
Met Arg Ala Phe Ser Ala Val Ala Ala Ala Leu Ala Leu Ser Trp
 1               5                  10                  15

Ala Ser Leu Ala Gln Ala Ala Arg Pro Arg Leu Val Pro Lys Pro Val
                20                  25                  30

Ser Arg Pro Ala Ser Ser Lys Ser Ala Ala Thr Thr Gly Glu Ala Tyr
            35                  40                  45

Phe Glu Gln Leu Leu Asp His His Asn Pro Glu Lys Gly Thr Phe Ser
        50                  55                  60

Gln Arg Tyr Trp Trp Ser Thr Glu Tyr Trp Gly Pro Gly Ser Pro
65                  70                  75                  80

Val Val Leu Phe Thr Pro Gly Glu Val Ser Ala Asp Gly Tyr Glu Gly
                85                  90                  95

Tyr Leu Thr Asn Gly Thr Leu Thr Gly Val Tyr Ala Gln Glu Ile Gln
            100                 105                 110

Gly Ala Val Ile Leu Ile Glu His Arg Tyr Trp Gly Asp Ser Ser Pro
        115                 120                 125

Tyr Glu Val Leu Asn Ala Glu Thr Leu Gln Tyr Leu Thr Leu Asp Gln
    130                 135                 140

Ala Ile Leu Asp Met Thr Tyr Phe Ala Glu Thr Val Lys Leu Gln Phe
145                 150                 155                 160

Asp Asn Ser Thr Arg Ser Asn Ala Gln Asn Ala Pro Trp Val Met Val
                165                 170                 175

Gly Gly Ser Tyr Ser Gly Ala Leu Thr Ala Trp Thr Glu Ser Val Ala
            180                 185                 190

Pro Gly Thr Phe Trp Ala Tyr His Ala Thr Ser Ala Pro Val Glu Ala
        195                 200                 205
```

```
Ile Tyr Asp Tyr Trp Gln Tyr Phe Tyr Pro Ile Gln Gln Gly Met Ala
    210                 215                 220

Gln Asn Cys Ser Lys Asp Val Ser Leu Val Ala Glu Tyr Val Asp Lys
225                 230                 235                 240

Ile Gly Lys Asn Gly Thr Ala Lys Glu Gln Gln Ala Leu Lys Glu Leu
                245                 250                 255

Phe Gly Leu Gly Ala Val Glu His Phe Asp Asp Phe Ala Ala Val Leu
            260                 265                 270

Pro Asn Gly Pro Tyr Leu Trp Gln Asp Asn Asp Phe Ala Thr Gly Tyr
        275                 280                 285

Ser Ser Phe Gln Phe Cys Asp Ala Val Glu Gly Val Glu Ala Gly
290                 295                 300

Ala Ala Val Thr Pro Gly Pro Glu Gly Val Gly Leu Glu Lys Ala Leu
305                 310                 315                 320

Ala Asn Tyr Ala Asn Trp Phe Asn Ser Thr Ile Leu Pro Asp Tyr Cys
                325                 330                 335

Ala Ser Tyr Gly Tyr Trp Thr Asp Glu Trp Ser Val Ala Cys Phe Asp
            340                 345                 350

Ser Tyr Asn Ala Ser Ser Pro Ile Tyr Thr Asp Thr Ser Val Gly Asn
        355                 360                 365

Ala Val Asp Arg Gln Trp Glu Trp Phe Leu Cys Asn Glu Pro Phe Phe
    370                 375                 380

Tyr Trp Gln Asp Gly Ala Pro Glu Gly Thr Ser Thr Ile Val Pro Arg
385                 390                 395                 400

Leu Val Ser Ala Ser Tyr Trp Gln Arg Gln Cys Pro Leu Tyr Phe Pro
                405                 410                 415

Glu Thr Asn Gly Tyr Thr Tyr Gly Ser Ala Lys Gly Lys Asn Ala Ala
            420                 425                 430

Thr Val Asn Ser Trp Thr Gly Gly Trp Asp Met Thr Arg Asn Thr Thr
        435                 440                 445

Arg Leu Ile Trp Thr Asn Gly Gln Tyr Asp Pro Trp Arg Asp Ser Gly
    450                 455                 460

Val Ser Ser Thr Phe Arg Pro Gly Gly Pro Leu Ala Ser Thr Ala Asn
465                 470                 475                 480

Glu Pro Val Gln Ile Ile Pro Gly Gly Phe His Cys Ser Asp Leu Tyr
                485                 490                 495

Met Ala Asp Tyr Tyr Ala Asn Glu Gly Val Lys Lys Val Val Asp Asn
            500                 505                 510

Glu Val Lys Gln Ile Lys Glu Trp Val Glu Glu Tyr Tyr Ala
        515                 520                 525

<210> SEQ ID NO 3
<211> LENGTH: 9
<212> TYPE: PRT
<213> ORGANISM: Aspergillus niger G306

<400> SEQUENCE: 3

Ala Thr Thr Gly Glu Ala Tyr Phe Glu
 1               5

<210> SEQ ID NO 4
<211> LENGTH: 26
<212> TYPE: DNA
<213> ORGANISM: Artificial Sequence
<220> FEATURE:
<221> NAME/KEY: modified_base
```

```
<222> LOCATION: 3, 6, 9, 12, 18
<223> OTHER INFORMATION: n = inosine
<220> FEATURE:
<223> OTHER INFORMATION: synthetic construct

<400> SEQUENCE: 4
gcnacnacng gngargcnta yttyga                                              26

<210> SEQ ID NO 5
<211> LENGTH: 26
<212> TYPE: DNA
<213> ORGANISM: Artificial Sequence
<220> FEATURE:
<221> NAME/KEY: modified_base
<222> LOCATION: 9, 15, 18, 21, 24
<223> OTHER INFORMATION: n = inosine
<220> FEATURE:
<223> OTHER INFORMATION: synthetic construct

<400> SEQUENCE: 5
tcraartang cytcnccngt ngtngc                                              26

<210> SEQ ID NO 6
<211> LENGTH: 14
<212> TYPE: PRT
<213> ORGANISM: Aspergillus niger G306

<400> SEQUENCE: 6

Ala Thr Val Asn Ser Trp Thr Gly Gly Trp Asp Phe Thr Arg
 1               5                  10

<210> SEQ ID NO 7
<211> LENGTH: 23
<212> TYPE: DNA
<213> ORGANISM: Artificial Sequence
<220> FEATURE:
<221> NAME/KEY: modified_base
<222> LOCATION: 6, 9, 12
<223> OTHER INFORMATION: n = inosine
<220> FEATURE:
<223> OTHER INFORMATION: synthetic construct

<400> SEQUENCE: 7
tggacnggng gntgggaytt yac                                                 23

<210> SEQ ID NO 8
<211> LENGTH: 23
<212> TYPE: DNA
<213> ORGANISM: Artificial Sequence
<220> FEATURE:
<221> NAME/KEY: modified_base
<222> LOCATION: 12, 15, 18
<223> OTHER INFORMATION: n = inosine
<220> FEATURE:
<223> OTHER INFORMATION: synthetic construct

<400> SEQUENCE: 8
gtraartccc anccnccngt cca                                                 23

<210> SEQ ID NO 9
<211> LENGTH: 9
<212> TYPE: PRT
<213> ORGANISM: Aspergillus niger G306

<400> SEQUENCE: 9

Asp Gly Ala Pro Glu Gly Thr Ser Thr
 1               5
```

```
<210> SEQ ID NO 10
<211> LENGTH: 20
<212> TYPE: DNA
<213> ORGANISM: Artificial Sequence
<220> FEATURE:
<221> NAME/KEY: modified_base
<222> LOCATION: 6, 9, 12, 18
<223> OTHER INFORMATION: n = inosine
<220> FEATURE:
<223> OTHER INFORMATION: synthetic construct

<400> SEQUENCE: 10
gayggngcnc cngarggnac                                                       20

<210> SEQ ID NO 11
<211> LENGTH: 20
<212> TYPE: DNA
<213> ORGANISM: Artificial Sequence
<220> FEATURE:
<221> NAME/KEY: modified_base
<222> LOCATION: 3, 9 12, 15
<223> OTHER INFORMATION: n = inosine
<220> FEATURE:
<223> OTHER INFORMATION: synthetic construct

<400> SEQUENCE: 11
gtnccytcng gngcnccrtc                                                       20

<210> SEQ ID NO 12
<211> LENGTH: 10
<212> TYPE: PRT
<213> ORGANISM: Aspergillus niger G306

<400> SEQUENCE: 12

Glu Arg Glu Ala Gly Ala Ala Val Thr Pro
 1               5                  10

<210> SEQ ID NO 13
<211> LENGTH: 23
<212> TYPE: DNA
<213> ORGANISM: Artificial Sequence
<220> FEATURE:
<221> NAME/KEY: modified_base
<222> LOCATION: 6, 9, 12, 15, 18, 21
<223> OTHER INFORMATION: n = inosine
<220> FEATURE:
<223> OTHER INFORMATION: synthetic construct

<400> SEQUENCE: 13
gargcnggng cngcngtnac ncc                                                   23

<210> SEQ ID NO 14
<211> LENGTH: 23
<212> TYPE: DNA
<213> ORGANISM: Artificial Sequence
<220> FEATURE:
<221> NAME/KEY: modified_base
<222> LOCATION: 3, 6, 9, 12, 15, 18
<223> OTHER INFORMATION: n = inosine
<220> FEATURE:
<223> OTHER INFORMATION: synthetic construct

<400> SEQUENCE: 14
ggngtnacng cngcnccngc ytc                                                   23

<210> SEQ ID NO 15
<211> LENGTH: 3290
<212> TYPE: DNA
```

<213> ORGANISM: Aspergillus niger CBS513.88

<400> SEQUENCE: 15

```
gagaggcaga aggagtcatt tatcacttgt attccaatgt attttccatt tatagatact      60
gcattcaaat gcaccgttta gcatagcatc ccacattcta tttcattcca atctcatgcc     120
attgccatcc ccggtattaa tttacttctc cgccttatct tgcaatcttg caatctcttt     180
ctcctcgtta tcacgcgttc ctgcaggcgc acctccgatg gcactgcagc cggagtcccc     240
gcggcgccgg cactactaaa gactaaagtg tctagtctag cctccaatgt gctcacctcc     300
atcagcatct catccattta tcttctgacg atgtcatctg caggctccac ccctccggc     360
cgccccgacg ctctccgacg gtgcacaaca atcaattctg cagtcacgct caagattcgt     420
ccctgccgga ctcctcatgc cgtgcctggt ttaatctatg caatggagta aggtagtatc     480
gcctagcagg agcggagttc ctgctgcgct cacgccatgg tgccggcgca gacataaatc     540
gctcgtttcc tccggcgctg gccgttctct cgagccagtt tgtctgttgt ggttgtagga     600
tcctctgttc ccctcgacag ctcacaatgc gttccttctc cgttgtcgct gccgcgtcac     660
tggcgctctc ttgggcgtct ctggcccagg ctgctcgccc ccgtcttgtg cccaagccta     720
tctctcggcc agcttcgagt aagtcggctg cgactacggg tgaggcttat tttgagcagc     780
tgctggacca tcacaacccg gagaagggaa cgttttccca gcggtactgg tggagtactg     840
aatactgggg tggacctggg tcaccggtgc gtctctgaca tttggtctta tgaccggcca     900
tattgaaact tagccggtgg caaggtccgc aatcatgagg aacattgctg attaaactag     960
gtggtcctct ttaaccctgg agaggtctct gccgatggct atgagggta tctcaccaac    1020
gatactctca ctggtgtcta tgcgcaggag atccagggtg ccgtcattct cattgaacgt    1080
gagtgtcact gctaccatgg aaaaaagaca ttcgctgatc gaccccaatc tagaccgcta    1140
ctggggcgac tcttcgcctt atgaggtgct caatgccgaa acactcagt atctcacact    1200
ggatcagtcc attctggaca tgacctactt cgccgagacg gtaaagctgc agttcgataa    1260
tagcagccgc agcaatgcgc agaatgctgt atgttacctt caccgctcta tgtttctgat    1320
aggtactgac aacgtagccc tgggtcatgg tcggtggctc atacagcggt gccttgacgg    1380
cttggaccga gtctatcgcg cctggaacgt tctgggctta ccatgccacc agtgcgcctg    1440
tggaggctat ctatgacttt gtaggtgtag cctgctcttg ttatctatac ttgcagctaa    1500
ccaagccagt ggcaatactt ctaccccatt cagcaaggta tggcacagaa ctgcagcaag    1560
gatgtgtctc tggtagccga gtatgtcgac aaaattggga agaatggaac tgccaaggaa    1620
cagcaggagc tcaaagaatt gtttggtctg ggagctgttg agcattacga tgactttgcc    1680
gcgtgagtac ttcaaagtct atagacgagc ttttctgaca ggaacagtgt cctgcccaac    1740
ggaccgtacc tctggcaaga caacgacttt gtcacaggat actcttcctt cttccagttc    1800
tgtgatgctg tcgaggtgag ttaccaccag attcctcttg attgaagcaa tatactaacg    1860
gacacagggt gtcgaagccg gcgcggcagt gaccccggc cccgagggcg tcggacttga    1920
aaaggccctg gccaactacg caaactggtt caattcaacc atactcccta actgtatttc    1980
accatctctt gtctcgttcc tctcccttat cctcccagac taacctagtg acagactgcg    2040
caagctacgg ctactggacc gacgaatgga gcgtcgcctg tttcgacagc tataatgcct    2100
cgagccccat cttcaccgac acctccgtgg gtaaccctgt cgaccgccaa tgggaatggt    2160
tcctctgcaa cgagccttc ttctggtggc aggagtgcgt accccttacc tcattcatga    2220
taacacacga acaattccac taacaaagat ccagcggtgc cccgagggga acctccacta    2280
```

```
ttgtgcccg gctcgtcagc gcctcctact ggcaacgcca atgcccgctc tacttccccg    2340
aagttaacgg ctacacgtac ggcagcgcga agggtaaaaa ctccgctacg gtgaacagct    2400
ggacgggtgg atgggatatg acccgcaaca cgacgcggtt gatctggacg aacgggtagg    2460
tctcccccta atttccgttg aatgtgatgt gaagataaac tcaatgctaa taaattgaga    2520
aggcaatatg acccctggcg cgactccggt gtgtcgagca cttccggcc cggtggtccg    2580 ctggttagca cggcgaacga acccgtgcag attattccgg gcgggttcca ttgctcggac    2640
ttgtatatgg aggattacta tgcgaatgag ggtgtgagga aggtggttga taatgaggtg    2700
aagcagatta aggagtgggt ggaggagtat tatgcttgat gaagatactg gtggacatat    2760
ggagtgtaca taagatgaat ggtcataaaa tgatgatggt agatacggct atggctgttg    2820
attagatggt cctttcgcat ttcctaatta ctgagcacgt gctccatggt atgggaagtg    2880
gagacgttgc tatatatatt gactgtcggg ctattgttca cggcgtagaa gctagacgct    2940
ttgtctatgt ggccttcact aaagaccgtg actctgccca gtcttccccc cttcgaggac    3000
ctggtattag ccaaacccac ccacaaacct aacaaagatc atcgtgacat tgaagtcact    3060
ctaggtactg ctggcgctga ttacagtggc tcaattcgaa catttcaaca gcacataagg    3120
gaagggtcgc ttcacttgct accttgatac gaaagcagcc acgcccaaca cttatagggg    3180
tgacaaccat cggcatgctg ggttatctac tatatctcct gattctgtgg atcctggaga    3240
tcgatctggt acactaatct actacaatgc atgtgaagta gggataggca                3290

<210> SEQ ID NO 16
<211> LENGTH: 1581
<212> TYPE: DNA
<213> ORGANISM: Aspergillus niger CBS513.88

<400> SEQUENCE: 16
atgcgttcct tctccgttgt cgctgccgcg tcactggcgc tctcttgggc gtctctggcc      60
caggctgctc gccccgtct tgtgcccaag cctatctctc ggccagcttc gagtaagtcg     120
gctgcgacta cgggtgaggc ttattttgag cagctgctgg accatcacaa cccgagaag     180 ggaacgtttt cccagcggta ctggtggagt actgaatact ggggtggacc tgggtcaccg     240
gtggtcctct ttaaccctgg agaggtctct gccgatggct atgagggta tctcaccaac     300 gatactctca ctggtgtcta tgcgcaggag atccagggtg ccgtcattct cattgaacac     360
cgctactggg gcgactcttc gccttatgag gtgctcaatg ccgaaacact tcagtatctc     420
acactggatc agtccattct ggacatgacc tacttcgccg agacggtaaa gctgcagttc     480
gataatagca gccgcagcaa tgcgcagaat gctccctggg tcatggtcgg tggctcatac     540
agcggtgcct tgacggcttg gaccgagtct atcgcgcctg gaacgttctg ggcttaccat     600
gccaccagtg cgcctgtgga ggctatctat gactttggc aatacttcta ccccattcag     660
caaggtatgg cacagaactg cagcaaggat gtgtctctgg tagccgagta tgtcgacaaa     720
attgggaaga atgaactgc caaggaacag caggagctca agaattgtt tggtctggga     780 gctgttgagc attacgatga ctttgccgct gtcctgccca acggaccgta cctctggcaa     840
gacaacgact ttgtcacagg atactcttcc ttcttccagt tctgtgatgc tgtcgagggt     900
gtcgaagccg gcgcggcagt gacccccggc cccgagggc tcggacttga aaaggccctg     960
gccaactacg caaactggtt caattcaacc atactcccta actactgcgc aagctacggc    1020
tactggaccg acgaatggag cgtcgcctgt ttcgacagct ataatgcctc gagcccatc     1080
```

-continued

```
ttcaccgaca cctccgtggg taaccctgtc gaccgccaat gggaatggtt cctctgcaac      1140
gagcctttct tctggtggca ggacggtgcc cccgagggaa cctccactat tgtgccccgg      1200
ctcgtcagcg cctcctactg gcaacgccaa tgcccgctct acttccccga agttaacggc      1260
tacacgtacg gcagcgcgaa gggtaaaaac tccgctacgg tgaacagctg gacgggtgga      1320
tgggatatga cccgcaacac gacgcggttg atctggacga acgggcaata tgacccctgg      1380
cgcgactccg gtgtgtcgag cactttccgg cccggtggtc cgctggttag cacggcgaac      1440
gaacccgtgc agattattcc gggcgggttc cattgctcgg acttgtatat ggaggattac      1500
tatgcgaatg agggtgtgag gaaggtggtt gataatgagg tgaagcagat taaggagtgg      1560
gtggaggagt attatgcttg a                                                1581
```

<210> SEQ ID NO 17
<211> LENGTH: 526
<212> TYPE: PRT
<213> ORGANISM: Aspergillus niger CBS513.88

<400> SEQUENCE: 17

```
Met Arg Ser Phe Ser Val Val Ala Ala Ala Ser Leu Ala Leu Ser Trp
  1               5                  10                  15

Ala Ser Leu Ala Gln Ala Ala Arg Pro Arg Leu Val Pro Lys Pro Ile
             20                  25                  30

Ser Arg Pro Ala Ser Ser Lys Ser Ala Ala Thr Thr Gly Glu Ala Tyr
         35                  40                  45

Phe Glu Gln Leu Leu Asp His His Asn Pro Lys Gly Thr Phe Ser
     50                  55                  60

Gln Arg Tyr Trp Trp Ser Thr Glu Tyr Trp Gly Gly Pro Gly Ser Pro
 65                  70                  75                  80

Val Val Leu Phe Asn Pro Gly Glu Val Ser Ala Asp Gly Tyr Glu Gly
                 85                  90                  95

Tyr Leu Thr Asn Asp Thr Leu Thr Gly Val Tyr Ala Gln Glu Ile Gln
            100                 105                 110

Gly Ala Val Ile Leu Ile Glu His Arg Tyr Trp Gly Asp Ser Ser Pro
        115                 120                 125

Tyr Glu Val Leu Asn Ala Glu Thr Leu Gln Tyr Leu Thr Leu Asp Gln
    130                 135                 140

Ser Ile Leu Asp Met Thr Tyr Phe Ala Glu Thr Val Lys Leu Gln Phe
145                 150                 155                 160

Asp Asn Ser Ser Arg Ser Asn Ala Gln Asn Ala Pro Trp Val Met Val
                165                 170                 175

Gly Gly Ser Tyr Ser Gly Ala Leu Thr Ala Trp Thr Glu Ser Ile Ala
            180                 185                 190

Pro Gly Thr Phe Trp Ala Tyr His Ala Thr Ser Ala Pro Val Glu Ala
        195                 200                 205

Ile Tyr Asp Phe Trp Gln Tyr Phe Pro Ile Gln Gln Gly Met Ala
    210                 215                 220

Gln Asn Cys Ser Lys Asp Val Ser Leu Val Ala Glu Tyr Val Asp Lys
225                 230                 235                 240

Ile Gly Lys Asn Gly Thr Ala Lys Glu Gln Gln Glu Leu Lys Glu Leu
                245                 250                 255

Phe Gly Leu Gly Ala Val Glu His Tyr Asp Asp Phe Ala Ala Val Leu
            260                 265                 270

Pro Asn Gly Pro Tyr Leu Trp Gln Asp Asn Asp Phe Val Thr Gly Tyr
        275                 280                 285
```

Ser Ser Phe Phe Gln Phe Cys Asp Ala Val Glu Gly Val Glu Ala Gly
    290                 295                 300

Ala Ala Val Thr Pro Gly Pro Glu Gly Val Gly Leu Glu Lys Ala Leu
305                 310                 315                 320

Ala Asn Tyr Ala Asn Trp Phe Asn Ser Thr Ile Leu Pro Asn Tyr Cys
            325                 330                 335

Ala Ser Tyr Gly Tyr Trp Thr Asp Glu Trp Ser Val Ala Cys Phe Asp
            340                 345                 350

Ser Tyr Asn Ala Ser Ser Pro Ile Phe Thr Asp Thr Ser Val Gly Asn
        355                 360                 365

Pro Val Asp Arg Gln Trp Glu Trp Phe Leu Cys Asn Glu Pro Phe Phe
    370                 375                 380

Trp Trp Gln Asp Gly Ala Pro Glu Gly Thr Ser Thr Ile Val Pro Arg
385                 390                 395                 400

Leu Val Ser Ala Ser Tyr Trp Gln Arg Gln Cys Pro Leu Tyr Phe Pro
                405                 410                 415

Glu Val Asn Gly Tyr Thr Tyr Gly Ser Ala Lys Gly Lys Asn Ser Ala
            420                 425                 430

Thr Val Asn Ser Trp Thr Gly Gly Trp Asp Met Thr Arg Asn Thr Thr
        435                 440                 445

Arg Leu Ile Trp Thr Asn Gly Gln Tyr Asp Pro Trp Arg Asp Ser Gly
    450                 455                 460

Val Ser Ser Thr Phe Arg Pro Gly Gly Pro Leu Val Ser Thr Ala Asn
465                 470                 475                 480

Glu Pro Val Gln Ile Ile Pro Gly Gly Phe His Cys Ser Asp Leu Tyr
                485                 490                 495

Met Glu Asp Tyr Tyr Ala Asn Glu Gly Val Arg Lys Val Val Asp Asn
            500                 505                 510

Glu Val Lys Gln Ile Lys Glu Trp Val Glu Glu Tyr Tyr Ala
        515                 520                 525

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
ttcagtactc caccagtacc tc                                          22

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
tgggaaaagg tgcccttctc c                                           21

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20

```
ggattatgat ggtccagcag c                                              21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
atgcgtgcct tctccgctgt c                                              21
```